(12) United States Patent
Pilch et al.

(10) Patent No.: US 12,061,201 B2
(45) Date of Patent: Aug. 13, 2024

(54) FLUORESCENT PROBES FOR THE VISUALIZATION OF FTSZ IN GRAM-POSITIVE AND GRAM-NEGATIVE BACTERIAL PATHOGENS

(71) Applicant: Rutgers, The State University of New Jersey, New Brunswick, NJ (US)

(72) Inventors: Daniel S. Pilch, New Brunswick, NJ (US); Edgar Ferrer-González, New Brunswick, NJ (US); Edmond J. LaVoie, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 448 days.

(21) Appl. No.: 17/027,513

(22) Filed: Sep. 21, 2020

(65) Prior Publication Data

US 2021/0088525 A1    Mar. 25, 2021

Related U.S. Application Data

(60) Provisional application No. 62/903,437, filed on Sep. 20, 2019.

(51) Int. Cl.
| | |
|---|---|
| *C07F 5/02* | (2006.01) |
| *G01N 33/52* | (2006.01) |
| *G01N 33/569* | (2006.01) |
| *G01N 33/58* | (2006.01) |

(52) U.S. Cl.
CPC ........... *G01N 33/582* (2013.01); *C07F 5/022* (2013.01); *G01N 33/52* (2013.01); *G01N 33/56911* (2013.01)

(58) Field of Classification Search
CPC ...... C07F 5/022; G01N 33/582; G01N 33/52; G01N 33/56911; C12Q 1/025
See application file for complete search history.

(56) References Cited

U.S. PATENT DOCUMENTS

2004/0161793 A1    8/2004    Trusca

FOREIGN PATENT DOCUMENTS

| WO | 2005046730 A2 | 5/2005 | | |
|---|---|---|---|---|
| WO | 2009095258 A1 | 8/2009 | | |
| WO | WO-2009095258 A1 * | 8/2009 | ................ | C12Q 1/02 |
| WO | WO-2012142671 A1 * | 10/2012 | ........... | A61K 31/166 |

OTHER PUBLICATIONS

Axis Pharm "Cyanine Dyes" (2018) (online). Retrieved on Aug. 13, 2022. Retrieved from <https://axispharm.com/product-category/fluorescent-probes/cyanine-dyes/>. (Year: 2018).*
Wikipedia "Cyanine" (Sep. 2018) Retrieved on Aug. 13, 2022. Retrieved from the Wayback Machine at <https://web.archive.org/web/20180330230755/https://en.wikipedia.org/wiki/Cyanine>. (Year: 2018).*
Stokes et al. "An Improved Small-Molecule Inhibitor of FtsZ with Superior In Vitro Potency, Drug-Like Properties, and In Vivo Efficacy" Antimicrob. Agents Chemother. 2013, 57, 317-325. (Year: 2013).*
Artola et al. "The structural assembly switch of cell division protein FtsZ probed with fluorescent allosteric inhibitors" Chem. Sci. 2017, 8, 1525. (Year: 2017).*
Artola, M. , et al., "The structural assembly switch of cell division protein FtsZ probed with fluorescent allosteric Inhibitors", Chem. Sci. 8, 1525-1534 (2017).
Beall, B. , et al., "FtsZ in Bacillus subtilis is required for vegetative septation and for asymmetric septation during sporulation", Genes & Development 5, 447-455 (1991).
Dai, K. , et al., "ftsZ is an Essential Cell Division Gene in *Escherichia coli*", Journal of Bacteriology 173(11), 3500-3506 (1991).
Ferrer-Gonzalez, E , et al., "Structure-Guided Design of a Fluorescent Probe for the Visualization of FtsZ in Clinically Important Gram-Positive and Gram-Negative Bacterial Pathogens", Scientific Reports 9, 20092, 1-16, Supplementary Information, 13 pages (2019).
Haydon, D. J, , et al., "An inhibitor of FtsZ with potent and selective anti-staphylococcal activity", Science 321, 1673-1675 (2008).
Haydon , et al., "Creating an antibacterial with in vivo efficacy: synthesis and characterization of potent inhibitors of the bacterial cell division protein FtsZ with improved pharmaceutical properties", J. Med. Chem 53, 3927-3936 (2010).
Hurley, K. A. , et al., "Targeting the Bacterial Division Protein FtsZ", J. Med. Chem. 59, 6975-6998 (2016).
Kaul, M , et al., "An FtsZ-Targeting Prodrug with Oral Antistaphylococcal Efficacy In Vivo", Antimicrobial Agents and Chemotherapy 57(12), 5860-5869 (2013).
Kaul, M. , et al., "Pharmacokinetics and in vivo antistaphylococcal efficacy of TXY 541, a 1-methylpiperidine-4-carboxamide prodrug of PC190723", Biochemical Pharmacology 86, 1699-1707 (2013).

(Continued)

*Primary Examiner* — Amanda L. Aguirre
(74) *Attorney, Agent, or Firm* — Viksnins Harris Padys Malen LLP

(57) ABSTRACT

The invention provides a compound of formula I:

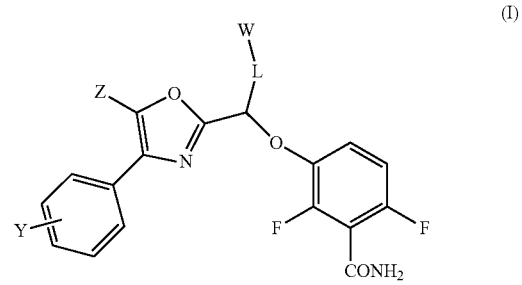

or a salt thereof, wherein Y, Z, L, and W have any of the values described in the specification, as well as compositions comprising a compound of formula I or a salt thereof. The compounds are useful as tools for visualizing FtsZ and monitoring cell division in a broad range of Gram-positive and Gram-negative bacterial pathogens of acute clinical importance and for identifying new FtsZ inhibitors.

18 Claims, 9 Drawing Sheets

(56) References Cited

OTHER PUBLICATIONS

Kaul, M , et al., "TXA709, an FtsZ-Targeting Benzamide Prodrug with Improved Pharmacokinetics and Enhanced In Vivo Efficacy against Methicillin- Resistant *Staphylococcus aureus*", Antimicrobial Agents and Chemotherapy 59 (8), 4845-4855 (2015).

Knudson, S. , et al., "A Trisubstituted Benzimidazole Cell Division Inhibitor with Efficacy against *Mycobacterium tuberculosis*", PLSO One 9, e93953 (2014).

Knudson, S. E. , et al., "Cell division inhibitors with efficacy equivalent to isoniazid in the acute murine *Mycobacterium tuberculosis* infection model", J. Antimicrob. Chemother 70(11), 3070-3073 (2015).

Kusuma, K. , et al., "FtsZ as an Antibacterial Target: Status and Guidelines for Progressing This Avenue", ACS Infect. Dis. 5, 1279-1294 (2019).

Lock, R. L. , et al., "Cell-division inhibitors: new insights for future antibiotics", Nat. Rev. Drug Disc. 7, 324-338 (2008).

Margalit, D. , et al., "Targeting cell division: Small-molecule inhibitors of FtsZ GTPase perturb cytokinetic ring assembly and induce bacterial lethality", Proc. Natl. Acad. Sci. USA 101, 11821-11826 (2004).

Matijasic, M , et al., "Fluorescently labeled macrolides as a tool for monitoring cellular and tissue distribution of azithromycin", Pharmacol Res 66 (4), 332-342 (2012).

Pinho, M. , et al., "Dispersed Mode of *Staphylococcus aureus* Cell Wall Synthesis in the Absence of the Division Machinery", Molecular Microbiology 50(3), 871-881 (2003).

Sass, P. , et al., "Bacterial cell division as a target for new antibiotics", Curr. Opin. Microbiol. 16, 522-530 (2013).

Stokes, N. , et al., "An Improved Small-Molecule Inhibitor of FtsZ with Superior In Vitro Potency, Drug-Like Properties, and In Vivo Efficacy", Antimicrobial Agents and Chemotherapy 57(1), 317-325 (2013).

Stokes, N. R. , et al., "Design, synthesis and structure-activity relationships of substituted oxazole-benzamide antibacterial inhibitors of FtsZ", Bioorg. Med. Chem. Lett. 24, 353-359 (2014).

Stone, M. R. L , et al., "Fluorescent Antibiotics: New Research Tools to Fight Antibiotic Resistance", Trends Biotechnol. 36(5), 523-536 (2018).

Stratton, C. , "Dead Bugs Don't Mutate: Susceptibility Issues in the Emergence of Bacterial Resistance", Emerging Infectious Diseases 9(1), 10-16 (2003).

Tan, C. M. , et al., "Restoring methicillin-resistant *Staphylococcus aureus* susceptibility to β-lactam antibiotics", Sci. Transl. Med. 4(126), 126ra35, 13 pages (2012).

Tereshchenkov, A , et al., "New fluorescent macrolide derivatives for studying interactions of antibiotics and their analogs with the ribosomal exit tunnel", Biochemistry (Moscow) 81, 1163-1172 (2016).

Tripathy, S. , et al., "FtsZ inhibitors as a new genera of antibacterial agents", Bioorg. Chem. 91,103169 (2019).

Ventola, C. , "The Antibiotic Resistance Crisis", The Antiboitic Resistance Crisis Part 1: Causes and Threats 40, 277-283 (2015).

World Health Organization , "Antibacterial Agents in Clinical Development: an Analysis of the Antibacterial Clinical Development Pipeline, Including Tuberculosis", 48 pages (2017).

World Health Organization , "Antimicrobial Resistance: Global Report on Surveillance", 1-235 (2014).

Ferrer-Gonzalez, E , et al., "Structure-Guided Design of a Fluorescent Probe for the Visualization of FtsZ in Clinically Important Gram-Positive and Gram-Negative Bacterial Pathogens", Scientific Reports 9, 20092, 1-16, Supplementary Information, 13 pages (2019). [Full document.].

* cited by examiner

FIGURES 9A-9L
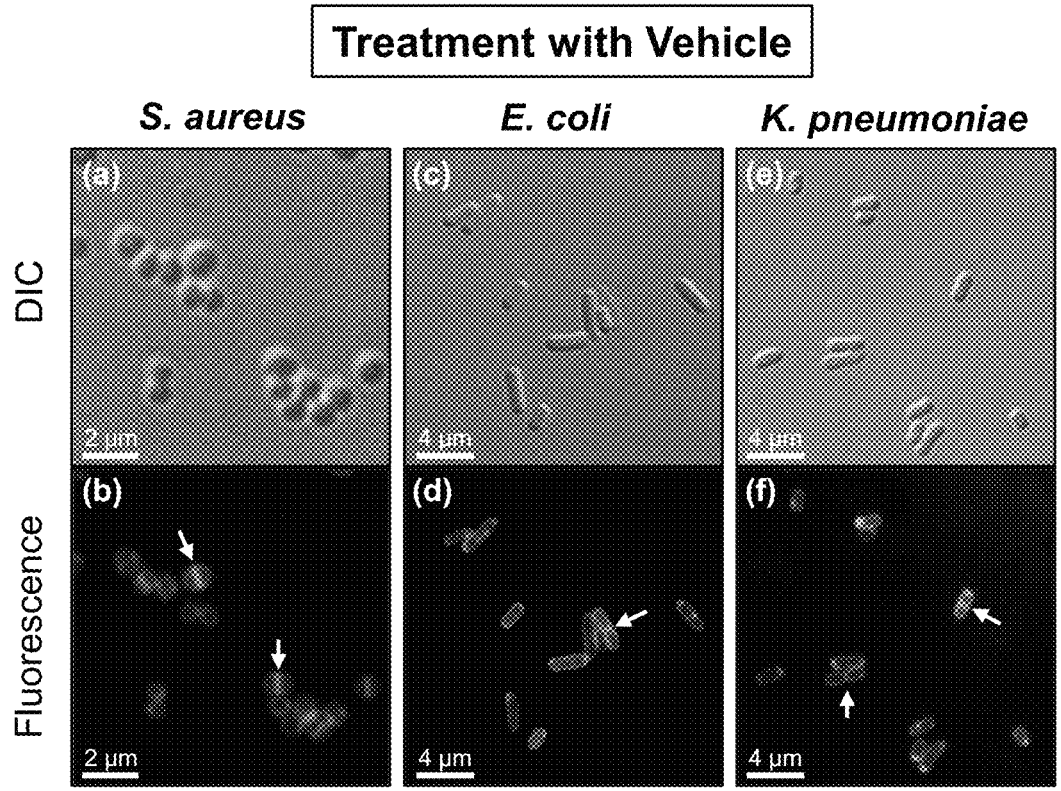
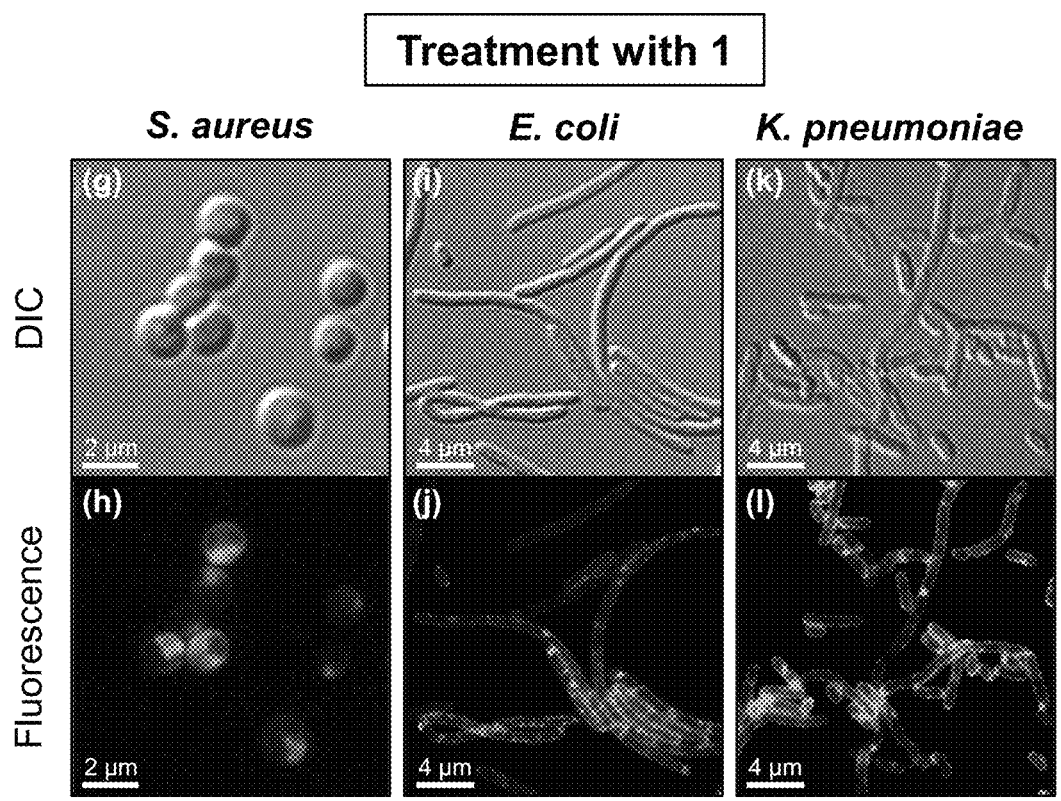

ns of action (Stone, M. R. L. et al., *Trends Biotechnol.* 36, 523-536 (2018)).

FLUORESCENT PROBES FOR THE VISUALIZATION OF FTSZ IN GRAM-POSITIVE AND GRAM-NEGATIVE BACTERIAL PATHOGENS

CROSS-REFERENCE TO RELATED APPLICATION

This application claims priority to U.S. Provisional Application No. 62/903,437 that was filed on Sep. 20, 2019. The entire content of the application referenced above is hereby incorporated by reference herein.

STATEMENT REGARDING FEDERALLY SPONSORED RESEARCH

This invention was made with government support under AI118874 awarded by National Institutes of Health. The government has certain rights in the invention.

BACKGROUND OF THE INVENTION

The discovery and development of antibiotics have saved millions of lives and revolutionized modern medicine (Ventola, C. L. The Antibiotic Resistance Crisis Part 1: Causes and Threats. P. T. 40, 277-283 (2015)). However, the alarming rise in multidrug-resistant (MDR) bacteria has threatened the usefulness of our current arsenal of antibiotics, leading the World Health Organization (WHO) to suggest an impending post-antibiotic era, where minor infections would become lethal (World Health Organization. *Antimicrobial Resistance: Global Report on Surveillance.* 232 pp. (World Health Organization, 2014)). A recent WHO report highlights the global magnitude of an ever-worsening crisis, exacerbated by a chronic shortage of antibiotics capable of treating infections cause by MDR pathogens. Currently, the majority of drug candidates in the antibiotic pipeline are derivatives of known antibiotics that will provide only a short-term solution to the problem (World Health Organization. *Antibacterial Agents in Clinical Development: An Analysis of the Antibacterial Clinical Development Pipeline, Including Tuberculosis.* 48 pp. (World Health Organization, 2017)). Furthermore, many of these drug candidates have limited or no activity against MDR Gram-negative bacterial pathogens, which are particularly problematic to treat.

Addressing the global antibiotic resistance problem requires the development of new drug chemotypes and the identification of new antibacterial drug targets. The filamentous temperature-sensitive Z (FtsZ) protein has been identified as a promising new target for the development of novel antibiotics (Lock, R. L. & Harry, E., J. *Nat. Rev. Drug Discov.* 7, 324-338 (2008); Sass, P. & Brotz-Oesterhelt, H., *Curr. Opin. Microbiol.* 16, 522-530 (2013); Kusuma, K. D., et al., *ACS Infect. Dis.* 5, 1279-1294 (2019); Haydon, D. J. et al., *J. Med. Chem.* 53, 3927-3936 (2010); Haydon, D. J. et al., An 321, 1673-1675 (2008); Kaul, M. et al., *Agents Chemother.* 57, 5860-5869 (2013); Kaul, M. et al., P *Biochem. Pharmacol.* 86, 1699-1707 (2013); Kaul, M. et al., *Antimicrob. Agents Chemother.* 59, 4845-4855 (2015); Stokes, N. R. et al., *Antimicrob. Agents Chemother.* 57, 317-325 (2013); Stokes, N. R. et al., *Bioorg. Med. Chem. Lett.* 24, 353-359 (2014); and Tan, C. M. et al., *Sci. Transl. Med.* 4, 126ra135 (2012)). FtsZ has several properties that make it an appealing antibacterial drug target. It is an essential protein required for bacterial division (Beall, B. & Lutkenhaus, J., *Genes Dev.* 5, 447-455 (1991); Dai, K. & Lutkenhaus, J., *J. Bacteriol.* 173, 3500-3506 (1991); and Pinho, M. G. & Errington, J., *Mol. Microbiol.* 50, 871-881 (2003)). Inhibition of FtsZ has a bactericidal rather than bacteriostatic effect (Haydon, D. J. et al., An 321, 1673-1675 (2008); and Kaul, M. et al., T *Antimicrob. Agents Chemother.* 59, 4845-4855 (2015)), a property that reduces the potential for emergence of future resistance (Stratton, C. W., *Emerg. Infect. Dis.* 9, 10-16 (2003)). FtsZ also has no functional human homolog, offering the potential to target this protein specifically with minimal toxicity (Stokes, N. R. et al., *Antimicrob. Agents Chemother.* 57, 317-325 (2013); and Tripathy, S. & Sahu, S. K., *Bioorg. Chem.* 91, 103169 (2019)). It is one of the most abundant and highly conserved cytoskeleton proteins among eubacteria (Hurley, K. A. et al. T, J., *Med. Chem.* 59, 6975-6998 (2016)), offering FtsZ inhibitors the potential for broad-spectrum antibacterial activity. Perhaps most importantly, FtsZ is a "druggable" target whose function can be disrupted by small molecule targeting of a single site on the protein.

Prodrugs of benzamide FtsZ inhibitors (PC190723 and TXA707) that are highly efficacious against infections caused by methicillin-resistant *Staphylococcus aureus* (MRSA) have been developed (Kaul, M. et al., *Agents Chemother.* 57, 5860-5869 (2013); Kaul, M. et al., P *Biochem. Pharmacol.* 86, 1699-1707 (2013); and Kaul, M. et al., *Antimicrob. Agents Chemother.* 59, 4845-4855 (2015)). One of these prodrugs (TXA709) is currently in phase I clinical trials (Kusuma, K. D., et al., *ACS Infect. Dis.* 5, 1279-1294 (2019)). To date, the bulk of the compounds that have been validated as FtsZ inhibitors both in vitro with purified FtsZ and in bacterial cells are associated with potent activity against staphylococci, *Mycobacterium tuberculosis* and selected other Gram-positive bacterial strains, but are weaker or have no activity against Gram-negative species (Haydon, D. J. et al., An 321, 1673-1675 (2008); Kaul, M. et al., *Antimicrob. Agents Chemother.* 59, 4845-4855 (2015); Stokes, N. R. et al., *Antimicrob. Agents Chemother.* 57, 317-325 (2013); Stokes, N. R. et al., *Bioorg. Med Chem. Lett.* 24, 353-359 (2014); Margalit, D. N., et al., *Proc. Natl. Acad. Sci. USA* 101, 11821-11826 (2004); and Knudson, S. E. et al. *PLoS One* 9, e93953 (2014)). Demonstration of in vivo efficacy among these FtsZ inhibitors has been limited almost exclusively to the treatment of *S. aureus* and *M. tuberculosis* infections (Haydon, D. J. et al., *J. Med. Chem.* 53, 3927-3936 (2010); Haydon, D. J. et al., An 321, 1673-1675 (2008); Kaul, M. et al., *Agents Chemother.* 57, 5860-5869 (2013); Kaul, M. et al., P *Biochem. Pharmacol.* 86, 1699-1707 (2013); Kaul, M. et al., *Antimicrob. Agents Chemother.* 59, 4845-4855 (2015); Stokes, N. R. et al., *Antimicrob. Agents Chemother.* 57, 317-325(2013); Tan, C. M. et al., *Sci. Transl. Med.* 4, 126ra35 (2012); Knudson, S. E. et al. *PLoS One* 9, e93953 (2014); and Knudson, S. E., et al. *J. Antimicrob. Chemother.* 70, 3070-3073 (2015)).

Advancing the development of new FtsZ inhibitors that can target a more expansive array of both Gram-positive and Gram-negative bacterial pathogens requires tools that allow screening for FtsZ inhibition in a broad range of bacterial species. Fluorescent antibiotics are useful tools for delineating the mechanisms underlying the antibacterial activities of compounds as well as the resistance phenotypes of bacteria (Stone, M. R. L. et al., *Trends Biotechnol.* 36, 523-536 (2018)). In addition, such tools can be used to screen for new antibiotic candidates with desired mechanisms of action (Stone, M. R. L. et al., *Trends Biotechnol.* 36, 523-536 (2018)).

Early efforts aimed at developing fluorescent FtsZ inhibitors were centered on analogs of the benzamide inhibitor PC190723 (Artola, M. et al., *Chem. Sci.* 8, 1525-1534

(2017)). Several of these fluorescent analogs were shown to bind FtsZ from both *S. aureus* and *Bacillus subtilis* (SaFtsZ and BsFtsZ, respectively), though the interactions were weak (with estimated $K_d$ values in the range of 11 to 29 μM for BsFtsZ at 25° C.). None of the analogs were able to bind FtsZ from *Escherichia coli* (EcFtsZ) to a significant degree (Artola, M. et al., *Chem. Sci.* 8, 1525-1534 (2017)). One analog was used to visualize FtsZ in *S. aureus* and *B. subtilis* cells (Artola, M. et al., *Chem. Sci.* 8, 1525-1534 (2017)), however, visualization required prolonged treatment with large concentrations of the analog (25 to 200 μM) and was lost upon pre-treatment with the parent inhibitor PC190723, limiting the usefulness of the analog as a screening tool for FtsZ inhibitors.

Currently, there is a need for new fluorescent FtsZ probes that overcome the limitations associated with the current derivatives. In particular, there is a need for probes that target the FtsZ proteins from clinically important Gram-negative pathogens (including *Escherichia coli, Klebsiella pneumoniae, Pseudomonas aeruginosa,* and *Acinetobacter baumannii*). Such probes would be useful for identifying new broad-spectrum FtsZ inhibitors as well as their mechanisms of action.

SUMMARY OF THE INVENTION

Applicant has identified fluorescent FtsZ probes that overcome one or more of the limitations associated with current FtsZ probes. In particular, applicant has identified probes that target the FtsZ proteins from clinically important Gram-negative pathogens (including *Escherichia coli, Klebsiella pneumoniae, Pseudomonas aeruginosa,* and *Acinetobacter baumannii*) with high affinity ($K_d$ values in the range of 0.22 to 0.82 μM). The probes are useful for visualizing FtsZ and monitoring cell division in a broad range of both Gram-positive and Gram-negative bacterial pathogens and for identifying new broad-spectrum FtsZ inhibitors.

Accordingly, in one aspect the invention provides a compound of formula I:

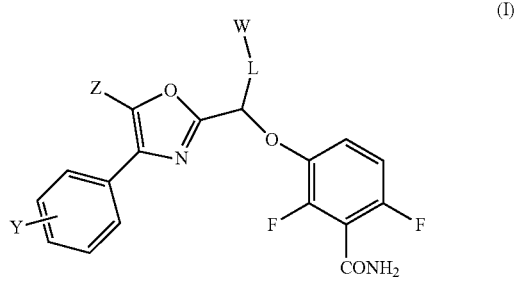

or a salt thereof, wherein:

Y is H, halo, halo($C_1$-$C_6$)alkyl, halo($C_1$-$C_6$)alkoxy, or CN;

L is a linking group;

Z is halo, cyano, or halo($C_1$-$C_6$)alkyl; and

W is a detectable group

The invention also provides a composition comprising a compound of formula (I) or a salt thereof, and a pharmaceutically acceptable excipient.

The invention also provides a method for visualizing FtsZ in live Gram-positive or Gram-negative bacterial cells comprising contacting the cell with a compound of formula (I) or a salt thereof.

The invention also provides a fluorescence microscopy assay for visualizing FtsZ in live Gram-positive or Gram-negative bacterial cells using fluorescent compounds of the invention. For visualizing FtsZ in Gram-positive bacteria, the bacterial cells can be grown to log-phase in media suitable for each individual pathogen being examined. For each Gram-positive bacterial strain, a total of 1 mL of cell culture is centrifuged at 15,000×g for 1 minute and washed 2-3 times with 1 mL of phosphate-buffered saline (PBS). After the final wash, the pelleted cells are resuspended in 500 μL of PBS containing 0.5-5 μg/mL of the fluorescent probe being used and incubated in the dark for 5 minutes at room temperature. The cells can then be centrifuged at 15,000×g for 1 minute, washed twice with 1 mL of PBS, and subsequently resuspended in 200 μL of PBS. 8 μL of this final cell suspension can then be spread on a 0.25 mm layer of 1.5% high-resolution agarose in PBS, which is mounted on a standard 75×25×1 mm microscope slide using a 1.7× 2.8×0.025 cm Gene Frame. A 24×40 mm cover slip can be then applied to the agarose pad to prepare the slide for microscopic visualization using a fluorescence microscope equipped with mercury lamp, a 100× oil immersion objective (1.40 aperture), and a filter appropriate for detecting the emission signal of the fluorescent probe being used. Images can be captured using a high-resolution charge-coupled device (CCD) camera and a corresponding imaging software package.

For visualizing FtsZ in Gram-negative bacteria, the bacterial cells can be grown to log-phase in media suitable for each individual pathogen being examined. For each Gram-negative bacterial strain, a total of 1 mL of cell culture can be centrifuged at 15,000×g for 1 minute and washed twice with 1 mL of Tris-buffered saline (TBS) composed of 50 mM Tris-HCl pH 7.6 and 150 mM NaCl. After the final wash, the pelleted cells can be resuspended in 500 μL of TBS containing 0.5-5 μg/mL of the fluorescent probe being used and pentamidine isethionate (at concentrations ranging from 0.5-5 mg/mL). The resuspended cells can be incubated in the dark for 5 minutes at room temperature, centrifuged at 15,000×g for 1 minute, washed twice with 1 mL of TBS, and subsequently resuspended in 200 μL of TBS. This final cell suspension can be prepared for microscopy as described above for the Gram-positive bacterial cells.

The invention also provides a method for identifying a FtsZ inhibitor

The invention also provides a fluorescence microscopy assay for visualizing the impact of potential FtsZ inhibitors in live Gram-positive and Gram-negative bacterial cells using compounds of the invention. To visualize the impact of treatment with test agents that have the potential to act as FtsZ inhibitors, the bacterial cells can be grown to log-phase in media suitable for each individual pathogen being examined and diluted to an $OD_{600}$ of 0.1. Each cell culture can be treated with either vehicle or the test agent at 2×-8× the minimal inhibitory concentration (MIC) for 3 hours at 37° C. Following this treatment, 1 mL of each culture can be centrifuged at 15,000×g for 1 minute and washed twice with 1 mL of PBS (for Gram-positive cells) or TBS (for Gram-negative cells). The resulting Gram-positive cell pellets can be further processed as described above for the Gram-positive bacterial strains and the resulting Gram-negative cell pellets can be further processed as described above for the Gram-negative bacterial strains. The impact of treatment with the test agent can be examined microscopically as described above. Test agents that are observed to specifically alter the localization of FtsZ and induce morphological changes consistent with impaired cell division can be identified as FtsZ inhibitors.

The invention also provides a compound of formula (I) or a pharmaceutically acceptable salt thereof for use in visualizing FtsZ in live Gram-positive or Gram-negative bacterial cells.

The invention also provides a compound of formula (I) or a pharmaceutically acceptable salt thereof for use in identifying a FtsZ inhibitor.

The invention also provides processes and intermediates disclosed herein that are useful for preparing a compound of formula (I) or a salt thereof.

The compounds and methods of the invention can be used to detect, identify, or monitor cell division in any bacterial species that divides in a FtsZ-dependent manner.

In the area of marine and aquatic microbiology, the invention also provides a method to detect, identify, or monitor cell division in marine or aquatic bacteria, including bacteria of the phylum Bacteroidetes.

In the area of skin and gut microbiomes, the invention also provides a method to detect, identify, or monitor cell division in skin or gut bacteria, including bacteria of the phyla Firmicutes and Bacteroidetes, Actinobacteria, and Proteobacteria.

In the area of food microbiology, the invention also provides a method to detect, identify, or monitor cell division in the main types of bacteria found in food, including *Campylobacter, Clostridium perfringens, Escherichia coli, Salmonella*, and *Listeria*.

BRIEF DESCRIPTION OF DRAWINGS

FIG. 9A-9L: Visualization of the impact of treatment with 1 on FtsZ localization in *S. aureus* NRS705, *E. coli* N43, and *K. pneumoniae* ATCC 10031. Differential interference contrast (DIC) and fluorescence micrographs of the indicated bacterial cells treated for 3 h with either DMSO vehicle (FIGS. 9a-f) or 1 (FIGS. 9g-l) at 4×MIC (2 μg/mL for *S. aureus* and 4 μg/mL for *E. coli* and *K. pneumoniae*). Just prior to visualization, cells were labeled for 5 min with 1 μg/mL BOFP in the absence (for *S. aureus*) or presence of pentamidine isethionate (at 0.875 mg/mL for *E. coli* and 3.5 mg/mL for *K. pneumoniae*). The arrows in 9b, 9d, and 9f highlight representative FtsZ Z-rings at midcell labeled by BOFP.

DETAILED DESCRIPTION OF THE INVENTION

Figure 1:
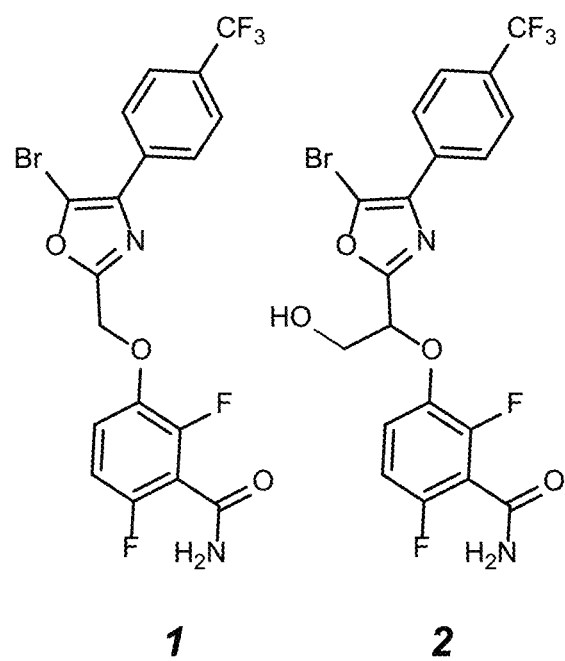
FIG. 1: Chemical structures of the oxazole-benzamide FtsZ inhibitors 1 and 2 (Stokes, N. R. et al., *Antimicrob. Agents Chemother.* 57, 317-325 (2013); and Stokes, N. R. et al., *Bioorg. Med. Chem. Lett.* 24, 353-359 (2014))

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $(C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "halo(alkyl)" as used herein refers to an alkyl group that is substituted with one or more independent halo groups (e.g. —$CF_3$, —$CF_2CF_3$, or —$CH_2CF_3$).

The term "halo(alkoxy)" as used herein refers to an alkoxy group that is substituted with one or more independent halo groups (e.g. —$OCF_3$, —$OCF_2CF_3$, or —$OCH_2CF_3$).

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line " $\sim$ " that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Linker.

As described herein, the detectable group W can be bonded (connected) to the remainder of the compound of formula (I) through an optional linker L. In one embodiment the linker is absent (e.g., the detectable group can be bonded (connected) directly to the remainder of the compound of formula (I)). The linker can be variable provided the compound of formula (I) functions as described herein. The linker can vary in length and atom composition and for example can be branched or non-branched or cyclic or a combination thereof. The linker may also modulate the properties of the compound of formula (I) such as but not limited to solubility, stability and aggregation.

Since the linkers used in the compound of formula (I) (e.g., linkers comprising polyethylene glycol (PEG)) can be highly variable, it is possible to use different sizes and types of detectable groups and still maintain the desired and/or optimal pharmacokinetic profile for the compound of formula (I).

In one embodiment the linker comprises about 3-5000 atoms. In one embodiment the linker comprises about 3-4000 atoms. In one embodiment the linker comprises about 3-2000 atoms. In one embodiment the linker comprises about 3-1000 atoms. In one embodiment the linker comprises about 3-750 atoms. In one embodiment the linker comprises about 3-500 atoms. In one embodiment the linker comprises about 3-250 atoms. In one embodiment the linker comprises about 3-100 atoms. In one embodiment the linker comprises about 3-50 atoms. In one embodiment the linker comprises about 3-25 atoms.

In one embodiment the linker comprises about 10-5000 atoms. In one embodiment the linker comprises about 10-4000 atoms. In one embodiment the linker comprises about 10-2000 atoms. In one embodiment the linker comprises about 10-1000 atoms. In one embodiment the linker comprises about 10-750 atoms. In one embodiment the linker comprises about 10-500 atoms. In one embodiment the linker comprises about 10-250 atoms. In one embodiment the linker comprises about 10-100 atoms. In one embodiment the linker comprises about 10-50 atoms. In one embodiment the linker comprises about 10-25 atoms.

In one embodiment the linker comprises atoms selected from H, C, N, S and O.

In one embodiment the linker comprises atoms selected from H, C, N, S, P and O.

In one embodiment the linker comprises a branched or unbranched, saturated or unsaturated, hydrocarbon chain, having from about 1 to 1000 (or 1-750, 1-500, 1-250, 1-100, 1-50, 1-25, 1-10, 1-5, 5-1000, 5-750, 5-500, 5-250, 5-100, 5-50, 5-25, 5-10 or 2-5 carbon atoms) wherein one or more of the carbon atoms is optionally replaced independently by —O—, —S, —N($R^a$)—, 3-7 membered heterocycle, 5-6-membered heteroaryl or carbocycle and wherein each chain, 3-7 membered heterocycle, 5-6-membered heteroaryl or carbocycle is optionally and independently substituted with one or more (e.g. 1, 2, 3, 4, 5 or more) substituents selected from ($C_1$-$C_6$)alkyl, ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, —N($R^a$)$_2$, hydroxy, oxo (=O), carboxy, aryl, aryloxy, heteroaryl, and heteroaryloxy, wherein each $R^a$ is independently H or ($C_1$-$C_6$)alkyl.

In one embodiment the linker comprises a branched or unbranched, saturated or unsaturated, hydrocarbon chain, having from about 1 to 1000 (or 1-750, 1-500, 1-250, 1-100, 1-50, 1-25, 1-10, 1-5, 5-1000, 5-750, 5-500, 5-250, 5-100, 5-50, 5-25, 5-10 or 2-5 carbon atoms) wherein one or more of the carbon atoms is optionally replaced independently by —O—, —S, —N($R^a$)—, wherein each $R^a$ is independently H or ($C_1$-$C_6$)alkyl.

In one embodiment the linker comprises a polyethylene glycol. In one embodiment the linker comprises a polyethylene glycol linked to the remainder of the compound of formula (I) by a carbonyl group. In one embodiment the polyethylene glycol comprises about 1 to about 500 or about 5 to about 500 or about 3 to about 100 repeat (e.g., —$CH_2CH_2O$—) units (Greenwald, R. B., et al., Poly (ethylene glycol) Prodrugs: Altered Pharmacokinetics and Pharmacodynamics, Chapter, 2.3.1., 283-338; Filpula, D., et al., Releasable PEGylation of proteins with customized linkers, Advanced Drug Delivery, 60, 2008, 29-49; Zhao, H., et al., Drug Conjugates with Poly(Ethylene Glycol), Drug Delivery in Oncology, 2012, 627-656).

In one embodiment the linker is L is —$CH_2CH_2C$(=O)O—$CH_2$—, —$CH_2C$(=O)O—$CH_2$, —C(=O)O—$CH_2$—, —O—$CH_2$—, or —$CH_2$—.

In one embodiment the invention provides a method for visualizing FtsZ in live Gram-positive or Gram-negative bacterial cells comprising treating the cells with a compound of formula (I) or a salt thereof, rinsing away unreacted compound, and measuring the fluorescence of the treated cells (e.g. using fluorescence microscopy), wherein the fluorescence signals are indicators of where FtsZ is located and distributed in the cells.

In one embodiment the invention provides a method for monitoring cell division live Gram-positive or Gram-negative bacterial cells comprising treating the cells with a compound of formula (I) or a salt thereof, rinsing away unreacted compound, and measuring the fluorescence of the treated cells (e.g. using fluorescence microscopy), wherein the fluorescence signals are indicators of where FtsZ is located and distributed in the cells. As FtsZ is an essential protein for cell division in almost all bacteria, it will be visible in the septa of all dividing cells, thereby enabling the identification and monitoring of cells that actively dividing.

In one embodiment the invention provides a method for identifying a FtsZ inhibitor comprising treating live Gram-positive or Gram-negative bacterial cells with a test FtsZ inhibitor, followed by treatment with a compound of formula (I) or a salt thereof, rinsing away unreacted compound, and measuring the fluorescence of the treated cells using fluorescence microscopy, wherein a fluorescence signal pattern in the cells treated with the test FtsZ inhibitor characterized by an enlarged phenotype and an absence of speta or septally-localized FtsZ is indicative of FtsZ inhibition and the disruption of cell division.

In one embodiment the invention provides a compound of formula (I) as described in any one of claims 1-17 or a salt thereof, for use in visualizing FtsZ in live Gram-positive or Gram-negative bacterial cells In one embodiment the invention provides a compound of formula (I) or a salt thereof, for use in monitoring cell division in live Gram-positive or Gram-negative bacterial cells, by treating the cells with a compound of formula (I) or a salt thereof, rinsing away unreacted compound, and measuring the fluorescence of the treated cells (e.g., using fluorescence microscopy), wherein the fluorescence signals are indicators of where FtsZ is located and distributed in the cells.

In one embodiment the invention provides a compound of formula (I) or a salt thereof, for use in identifying a FtsZ inhibitor, for example, by treating live Gram-positive or Gram-negative bacterial cells with a test FtsZ inhibitor, followed by treatment with a compound of formula (I) or a salt thereof, rinsing away unreacted compound, and measuring the fluorescence of the treated cells (e.g., using fluorescence microscopy}, wherein a fluorescence signal pattern in the cells treated with the test FtsZ inhibitor characterized by an enlarged phenotype and an absence of septa or septally-localized FtsZ is indicative of FtsZ inhibition and the disruption of cell division.

Detectable Group

In certain embodiments, the detectable group comprises a fluorescent group. A fluorescent group is also called a "fluorescent tag" or a "fluorophore". A fluorophore is a molecule that absorbs light (i.e., excites) at a characteristic wavelength and emits light (i.e. fluoresces and emits a signal) at a second lower-energy wavelength. The detectable agent may include, but is not limited to, one or more of the following fluorescent groups: fluorescein, tetrachlorofluorescein, hexachlorofluorescein, tetramethylrhodamine, rhodamine, cyanine-derivative dyes, Texas Red, Bodipy, and Alexa dyes. Examples of certain fluorophores include, e.g., FITC, GFP, 488 B, Brilliant Blue 515, CFSE, 7-AAD, PerCP, PerCP-Cy5-5, 488 A, PerCP-eFluor 710, SSC, APC-Cy7, APC-H7, 640A, APC-Alexa Fluor 750, APC-eFluor 780, Alexa Fluor 647, APC, 640 C, Sytox Red, Alexa Fluor 700, 640 B, Qdot 705, 405 B, Brilliant Violet 711, Qdot 605, 405 D, Brilliant Violet 605, eFluor 605, Pacific Blue, 405 F, Brilliant Violet 421, DyeCycle Violet, eFluor 450, Horizon v450, Qdot 800, 405 A, Brilliant Violet 786, Qdot 655, 405 C, Brilliant Violet 650, eFluor 650, Pacific Orange, 405 E, Brilliant Violet 510, Horizon v500, L/D Fixable Aqua, PE-Cy7, 561 A, DsRed, PE, 561 C, Cy3, tdTomato, PE-CF594, PE-Texas Red, PI, 561 B, mCherry, PE-Alexa Fluor, 355 B, Brilliant Ultraviolet 737, Alexa Fluor 350, 355 D, Brilliant Ultraviolet 395, 355 A, Brilliant Ultraviolet 805, 355 C and Brilliant Ultraviolet 496. Characteristic absorption and emission wavelengths for each of these are well known.

In certain embodiments, the detectable group comprises a chelating group, which may be labeled with a radionuclide. Any suitable chelating group can be employed. Suitable chelating groups are disclosed, e.g., in Rockey et al., Bioorganic & Medicinal Chemistry 19 (2011) 4080-4090; Poster Sessions, Proceedings of the 46$^{th}$ Annual Meeting, J. Nuc. Med., p. 316, No. 1386; Scientific Papers, Proceedings of the 46$^{th}$ Annual Meeting, J. Nuc. Med., p. 123, No. 499; Scientific Papers, Proceedings of the 46$^{th}$ Annual Meeting, J. Nuc. Med., p. 102, No. 413; Scientific Papers, Proceedings of the 46$^{th}$ Annual Meeting, J. Nuc. Med., p. 102, No. 414; Scientific Papers, Proceedings of the 46$^{th}$ Annual Meeting, J. Nuc. Med., p. 103, No. 415; Poster Sessions, Proceedings of the 46$^{th}$ Annual Meeting, J. Nuc. Med., p. 318, No. 1396; Poster Sessions, Proceedings of the 46$^{th}$ Annual Meeting, J. Nuc. Med., p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); C. J. Anderson et al., J. Nucl. Med. 36, 850 (1995); U.S. Pat. Nos. 5,739,313; and 6,004,533.

The detectable group can be linked to the remainder of a compound of formula (I) through any synthetically feasible position, provided the resulting compound of formula (I) or the salt thereof has the requisite properties to function as a probe.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific L comprises about 3-25 atoms.

A specific L is a branched or unbranched, saturated or unsaturated, hydrocarbon chain, having from about 1 to 25 carbon atoms, wherein one or more of the carbon atoms is optionally replaced independently by —O—, —S, —N($R^a$)—, 3-7 membered heterocycle, 5-6-membered heteroaryl or carbocycle and wherein each chain, 3-7 membered heterocycle, 5-6-membered heteroaryl or carbocycle is optionally and independently substituted with one or more (e.g. 1, 2, 3, 4, 5 or more) substituents independently selected from the group consisting of $(C_1-C_6)$alkyl, $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, —N($R^a$)$_2$, hydroxy, oxo (=O), carboxy, aryl, aryloxy, heteroaryl, and heteroaryloxy, wherein each $R^a$ is independently H or $(C_1-C_6)$alkyl.

A specific L is a branched or unbranched, saturated or unsaturated, hydrocarbon chain, having from about 1 to 15 carbon atoms, wherein one or more of the carbon atoms is optionally replaced independently by —O— or N($R^a$)—, and wherein each carbon atom is optionally substituted with one or more (e.g. 1, 2, 3, 4, 5 or more) substituents independently selected from the group consisting of $(C_1-C_6)$alkyl, $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, azido, cyano, halo, —N($R^a$)$_2$, hydroxy, oxo (=O), and carboxy, wherein each $R^a$ is independently H or $(C_1-C_6)$alkyl.

A specific L is a branched or unbranched, saturated hydrocarbon chain, having from about 1 to 15 carbon atoms, wherein one or more of the carbon atoms is optionally replaced independently by —O— or N($R^a$)—, and wherein each carbon atom is optionally substituted with one or more (e.g. 1, 2, 3, 4, 5 or more) substituents independently selected from the group consisting of halo and oxo (=O), wherein each $R^a$ is independently H or $(C_1$-$C_6)$alkyl.

A specific L is —CH$_2$CH$_2$C(=O)O—CH$_2$—, —CH$_2$C(=O)O—CH$_2$, —C(=O)O—CH$_2$—, —O—CH$_2$—, or —CH$_2$—.

In one embodiment, Y is halo, CF$_3$, OCF$_3$, OCF$_2$CF$_3$, or CN.

In one embodiment, Y is H, halo, CF$_3$, OCF$_3$, OCF$_2$CF$_3$, or CN.

In one embodiment, Z is halo, cyano, or trifluoromethyl.

A specific compound or salt is a compound of formula (Ia):

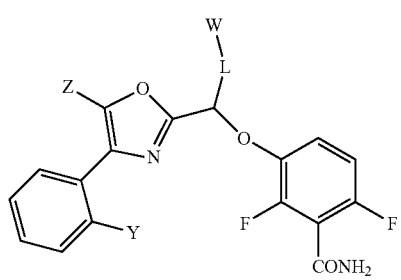

(Ia)

or a salt thereof.

A specific compound or salt is a compound of formula (Ib):

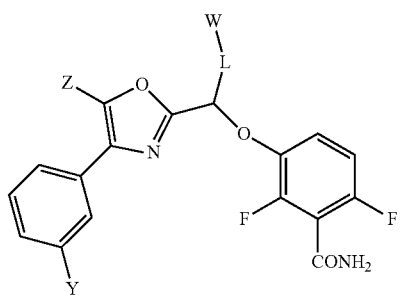

(Ib)

or a salt thereof.

A specific compound or salt is a compound of formula (Ic):

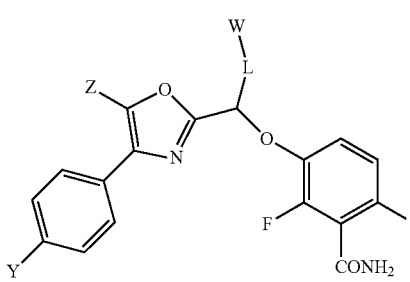

(Ic)

or a salt thereof.

A specific compound or salt is a compound of formula (Id):

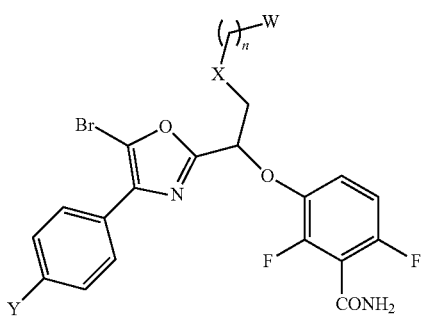

(Id)

or a salt thereof, wherein:
Y is H, halo, CF$_3$, OCF$_3$, OCF$_2$CF$_3$, or CN;
X is —O—, —C(=O)—, —OC(=O)—, —C(=O)O—, —N(R$^a$)C(=O)—, —C(=O)N(R$^a$)—, —OC(=O)O—, —OC(=O)O—, —N(R$^a$)C(=O)O—, —OC(=O)N(R$^a$)—, —N(R$^a$)—, —S—, —SC(=O)—, —C(=O)S—, —SC(=O)O—, —OC(=O)S—, —N(R$^a$)SO$_2$—, or —SO$_2$N(R$^a$)—;
n is 0, 1, 2, 3, 4, 5, or 6;
each $R^a$ is independently H or $(C_1$-$C_6)$alkyl; and
W is a detectable group.

A specific compound or salt is a compound of formula (Ie):

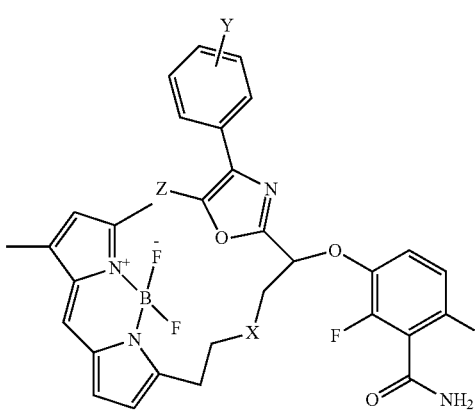

(Ie)

or a salt thereof.

A specific compound or salt is a compound of formula (If):

(If)

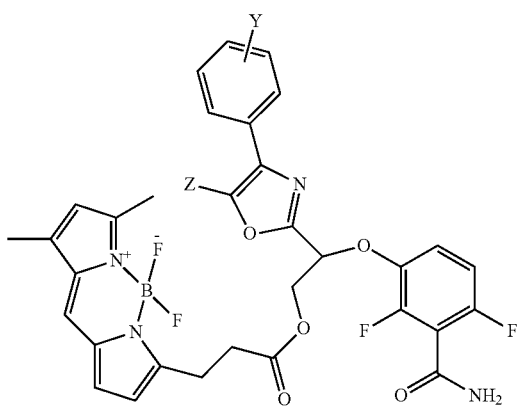

or a salt thereof.

A specific compound or salt is a compound of formula (Ig):

(Ig)

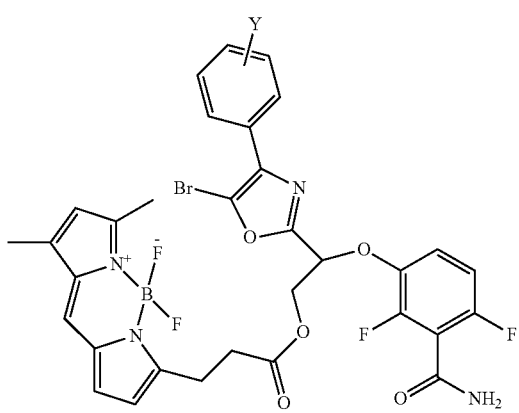

or a salt thereof.

A specific compound or salt is a compound of formula (Ih):

(Ih)

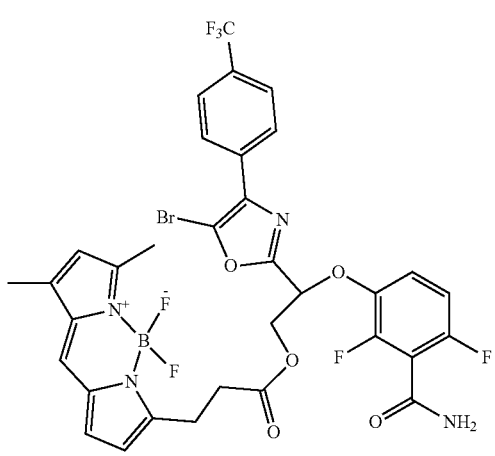

or a salt thereof.

A specific W comprises fluorescein, tetrachlorofluorescein, hexachlorofluorescein, tetramethylrhodamine, rhodamine, cyanine-derivative dyes, Texas Red, Bodipy, or an Alexa dye.

A specific W comprises a fluorophore from one of the following families:

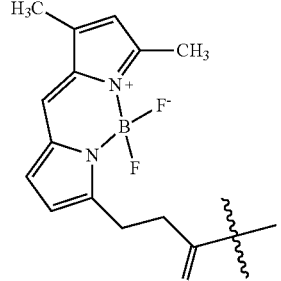

BIODIPY-FL

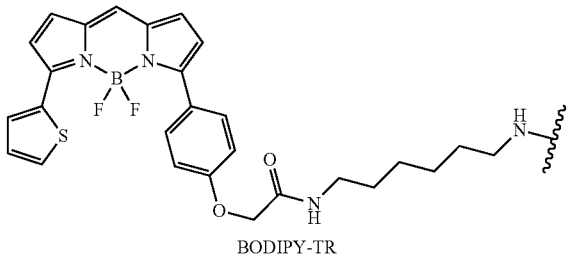

BODIPY-TR

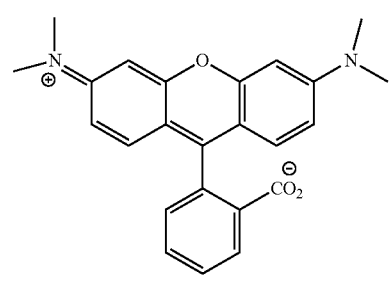

TMR

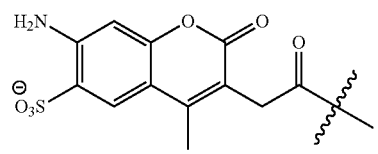

Alexa Fluor® 350

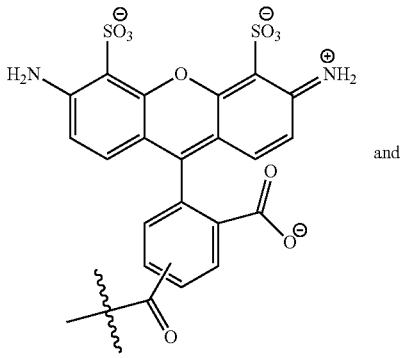

and

Alexa Fluor® 488 invention. A general coupling reaction between a substituted phenyl oxazole and BODIPY-FL reactant is illustrated below:

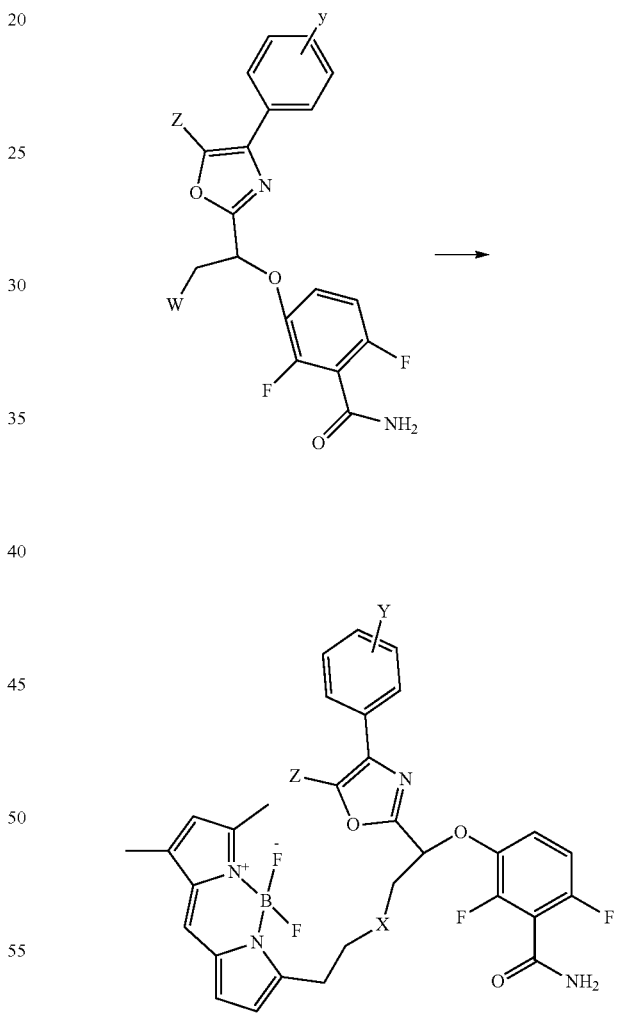

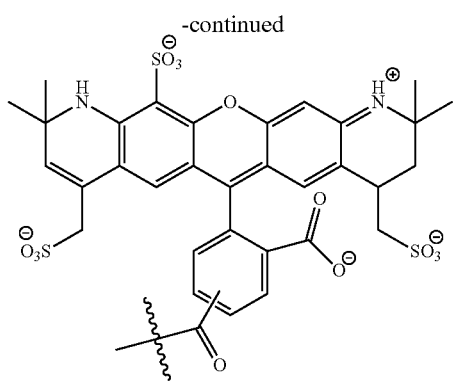

Alexa Fluor® 568

A specific W comprises a fluorophore from one of the following families:

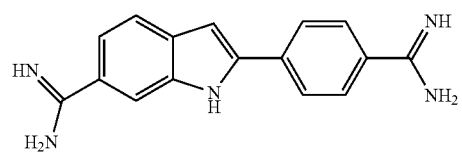

DAPI

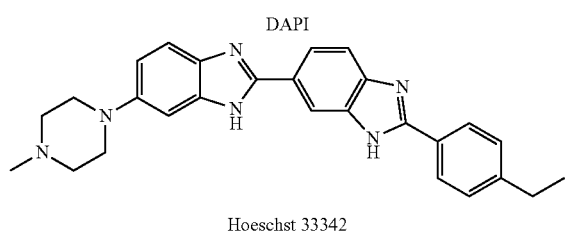

Hoeschst 33342

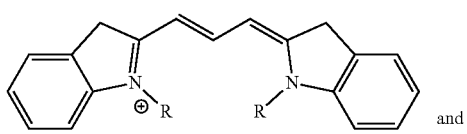

Cy3 and

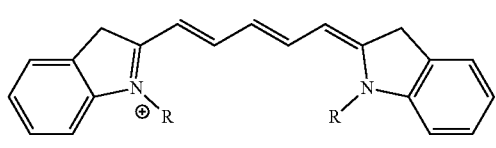

Cy5

Processes for preparing compounds of formula (I) are provided as further embodiments of the invention and are illustrated by the following procedures in which the meanings of the generic radicals are as given above unless otherwise qualified. The preparation of compounds of formula (I) and the preparation of synthetic intermediates that can be used to prepare compounds of formula (I) are illustrated in the following Schemes.

There are several literature procedures for preparing phenyl oxazole intermediates that can be coupled with a detectable group (e.g. a fluorophore) to provide compounds of the invention. Other suitable procedures for preparing phenyl oxazole intermediates that can be coupled with a detectable group (e.g. a fluorophore) to provide compounds of the invention are illustrated in Scheme 1 and Scheme 2.

Scheme 1
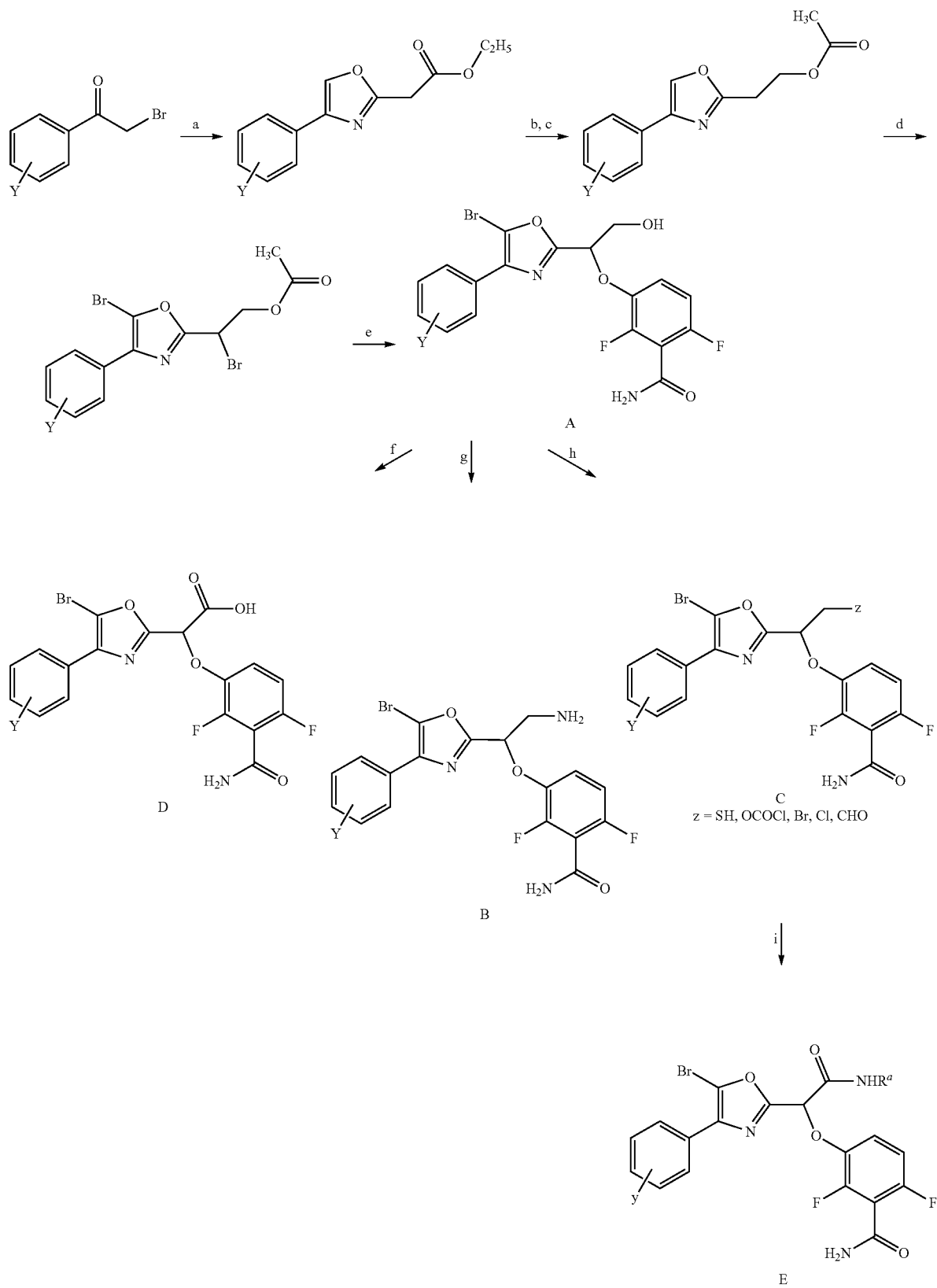

a) ethylmalonate; b) NaBH₄; c) acetic anhydride; d) NBS; e) 2,6-difluorobenzamide; f) CrO₃, H₂SO₄; g) methanesulfonyl chloride, then RNH₂; h) for example, PBr₃, Cl₃OCONH₂ or NBS; i) oxalyl chloride, ammonium acetate.

electrophiles that will react with nucleophiles. For BODIPY FL, for example, the NHS ester, the STP ester, and the SSE ester are designed to prepare conjugates with amines such as Compound B in Scheme 1.

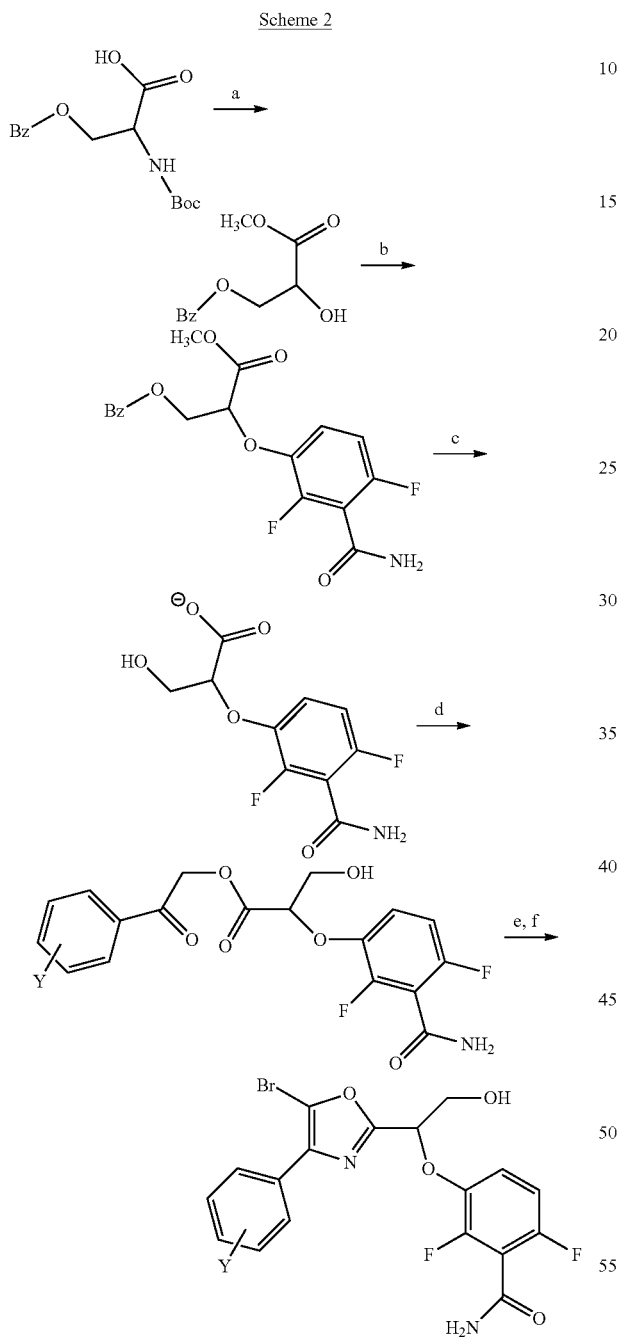

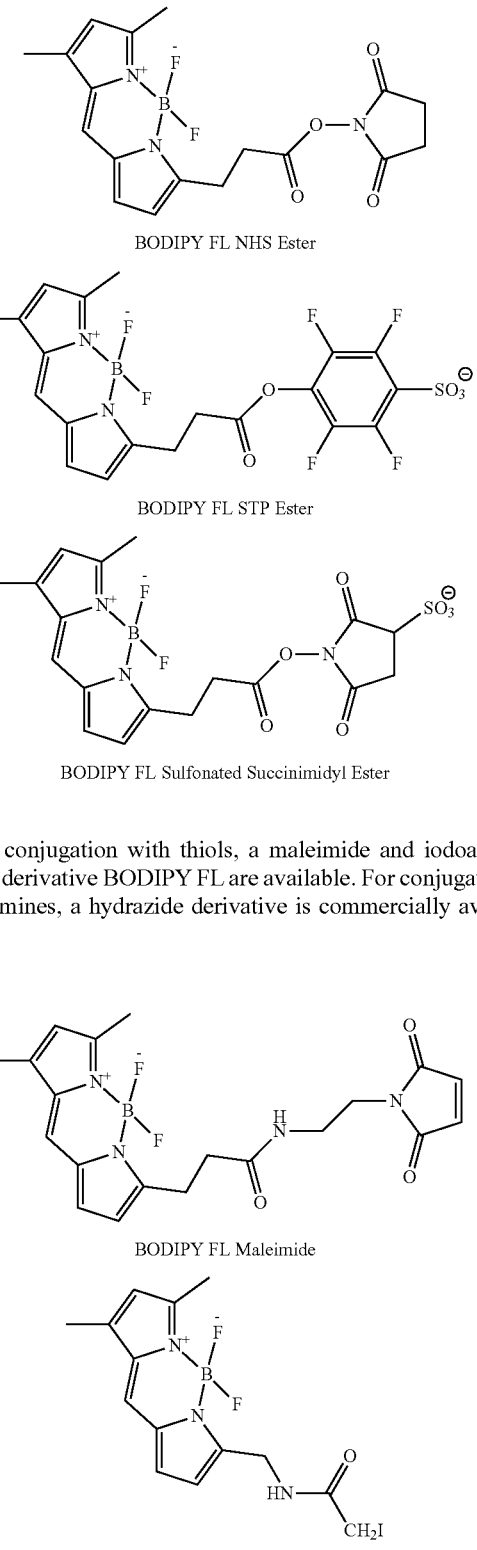

For conjugation with thiols, a maleimide and iodoacetamide derivative BODIPY FL are available. For conjugation with amines, a hydrazide derivative is commercially available.

a) NaNO₂, then triethylformate, H₂SO₄ b) Ph₃P, diethyldiazodicarboxylate, 2,6-difluoro-3-hydroxybenzamide, triethylamine; c) 20% Pd(OH)₂ on C, H₂; d) CeCO₃, H₂O; d) 3-bromo-1-(X-Phenyl)ethenone; e) acetamide, BF₃·Et₂O; f) Br₂ in CH₂Cl₂.

There are various analogs of the fluorophore families. Each of these analogs is designed to work directly as an electrophile for various nucleophiles or to be converted to

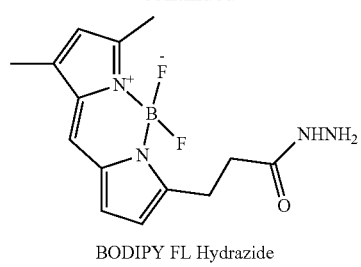

BODIPY FL Hydrazide

Additionally, as illustrated in Scheme 3, a BODIPY FL carboxylate can be used with a condensing agent (e.g., 1-ethyl-3-(3-dimethylaminopropyl)carbodiimide, EDC) for the formation of conjugates with alcohols, such as Compound A in Scheme 1.

Scheme 3

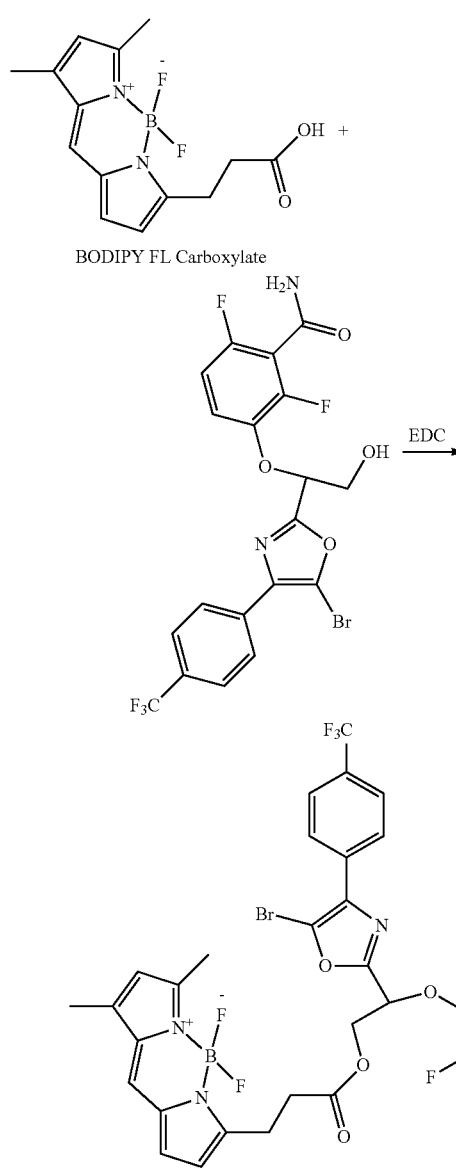

Additionally, compounds can be prepared as illustrated in Scheme 4.

Scheme 4

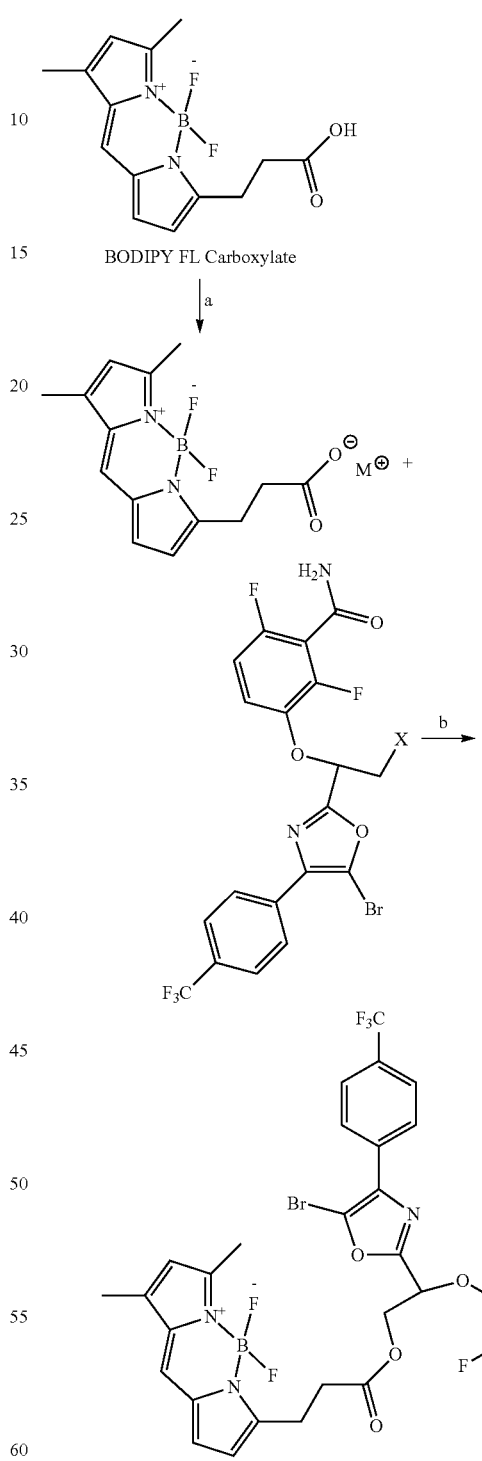

a) $Cs_2CO_3$ in methyl ethyl ketone (M+ is preferably Cs, However, the K and Na salts as formed through their carbonates can be used); b) methyl ethyl ketone, 65° C. (other polar aprotic solvents such as acetone or DMF or DMSO could be used), X is a halide or any other leaving group. For Example, see Dijkstra, G.; Kruizinga, W. H., Kellogg, R. M., *J. Org. Chem.* 1987, 52, 4230-4234.

Activated intermediates of other detectable groups (e.g. fluorophores) are known or are commercially available.

In cases where compounds are sufficiently basic or acidic, a salt of a compound of formula I can be useful as a probe or as an intermediate for isolating or purifying a compound of formula I.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The invention will now be illustrated by the following non-limiting Examples.

EXAMPLES

Figure 2:
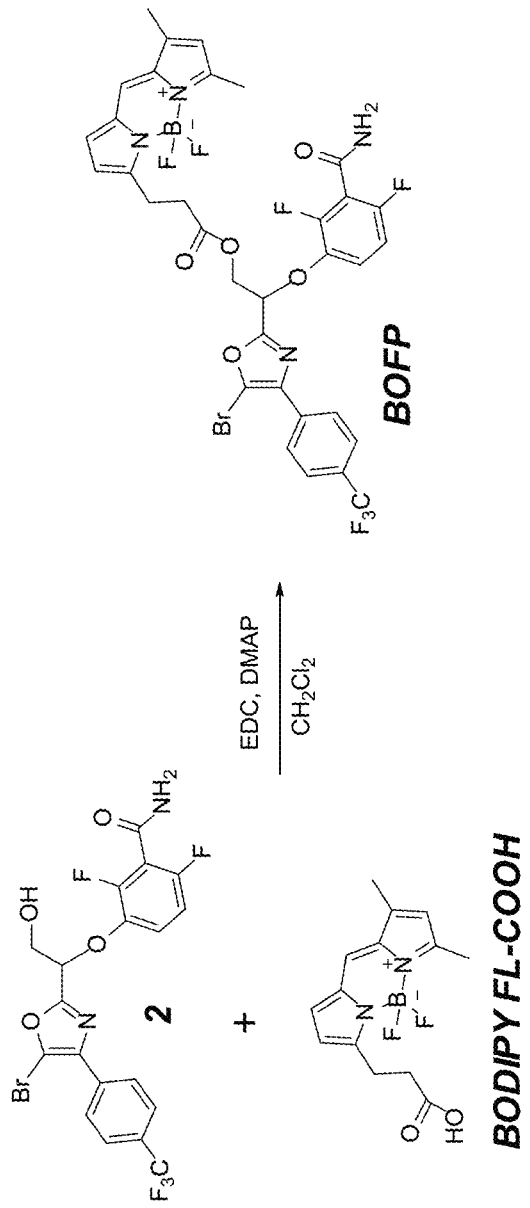
FIG. 2. Scheme for the synthesis of BOFP by reacting 2 with BODIPY FL-COOH in $CH_2Cl_2$ containing 1-ethyl-3-(3-dimethylaminopropyl)carbodiimide (EDC) and 4-dimethylaminopyridine (DMAP).

Example 1. BOFP, a BODIPY-Conjugated Fluorescent Derivative of 1 that Binds SaFtsZ with Affinity in the $K_d$ Range of 0.88 to 3.14 µM BOFP, a fluorescent analog of 1 (whose structure is shown in FIG. 1) in which a BODIPY fluorophore is conjugated to a desired site on the linker of 1, was designed and synthesized as schematically depicted in FIG. 2 and detailed below in Example 2.

Initial FtsZ-targeting characterizations of BOFP sought to determine whether this ligand could bind *S. aureus* FtsZ (SaFtsZ). Toward this end, fluorescence anisotropy was used to monitor the interaction of BOFP with SaFtsZ at three different temperatures (15, 25, and 37° C.). Significantly, the fluorescence anisotropy (r) of BOFP increases markedly with added SaFtsZ (FIG. 3), indicating the presence of a binding interaction. Analysis of the r-based binding isotherms with the 1:1 binding formalism embodied by Eq. 1 yielded excellent fits of the experimental data points (depicted by the solid curves in FIG. 3) and the corresponding $K_d$ values listed in Table 1, which ranged from 0.88±0.08 µM at 15° C. to 3.14±0.13 µM at 37° C. These results indicate that BOFP is not only able to bind SaFtsZ, but does so with a robust affinity in the sub- to low-micromolar $K_d$ range.

The binding of BOFP to SaFtsZ does not require the presence of GTP or magnesium. The filamentation of SaFtsZ requires the presence of both GTP and magnesium (Rivas, G. et al., *J. Biol. Chem.* 275, 11740-11749 (2000)). Neither of these reagents was present in the fluorescence anisotropy binding studies depicted in FIG. 3, indicating that the binding of BOFP to SaFtsZ does not require the presence of either GTP or magnesium. This observation markedly contrasts the previously reported fluorescence anisotropy studies by Artola, M. et al., *Chem. Sci.* 8, 1525-1534 (2017), which demonstrated that fluorescent analogs of the benzamide FtsZ inhibitor PC190723 required both GTP and magnesium in order to bind SaFtsZ. For comparative purposes, an investigation was carried out to determine whether the presence of a non-hydrolyzable analog of GTP (GMPCPP) and magnesium exerted an impact on the binding of BOFP to SaFtsZ, as reflected by a change in fluorescence anisotropy. At identical concentrations of BOFP and SaFtsZ (0.1 and 10 µM, respectively), the presence of neither GMPCPP alone (at 0.1 mM) nor MgCl$_2$ alone (at 10 mM) has a significant effect on the anisotropy of SaFtsZ-bound BOFP (FIG. 4), confirming that the binding of BOFP to SaFtsZ is independent of either GTP or magnesium. The presence of both GMPCPP and MgCl$_2$ results in a modest increase in the anisotropy of bound BOFP (FIG. 4), which likely reflects the filamentation of BOFP-bound SaFtsZ induced by the combination of GMPCPP and magnesium.

BOFP can target the FtsZ proteins from a broad range of clinically important Gram-positive bacterial pathogens, including enterococcal and streptococcal species. In addition to SaFtsZ, the ability of BOFP to target the FtsZ proteins from other Gram-positive bacterial pathogens, including *E. faecalis* (EfsFtsZ) *E. faecium* (EfmFtsZ), *S. pyogenes* (SpyFtsZ), *S. agalactiae* (SagFtsZ), and *S. pneumoniae* (SpnFtsZ) was investigated. Fluorescence anisotropy studies conducted at 15, 25, and 37° C. reveal that addition of each of the five target FtsZ proteins increases the anisotropy of BOFP significantly (FIGS. 5a-5e), indicative of a binding interaction between the probe and each of the host proteins. Thus, BOFP can target not only SaFtsZ, but also the FtsZ proteins from a broad range of other clinically important Gram-positive pathogens. Analysis of the anisotropy isotherms in FIG. 5 with Eq. 1 yielded outstanding fits of the experimental data points (as depicted by the solid curves), with the $K_d$ values derived from these fits being listed in Table 1. $K_d$ values for BOFP binding to the Gram-positive FtsZ proteins ranged from 1.72±0.06 µM at 15° C. to 4.62±0.12 µM at 37° C. for EfsFtsZ, 2.50±0.14 µM at 15° C. to 3.14±0.22 µM at 37° C. for EfmFtsZ, 0.91±0.06 µM at 15° C. to 1.55±0.08 µM at 37° C. for SpyFtsZ, 0.62±0.05 µM at 15° C. to 1.31±0.04 µM at 37° C. for SagFtsZ, and 3.02±0.30 µM at 15° C. to 3.81±0.69 µM at 37° C. for SpnFtsZ. These $K_d$ ranges are similar in magnitude to that observed for SaFtsZ. Artola et al. demonstrated the binding of their early-generation fluorescent FtsZ inhibitors only to SaFtsZ and BsFtsZ, while reporting $K_d$ values in the range of 11 to 29 µM for BsFtsZ at 25° C.[25]. Significantly, the lower range of $K_d$ values observe for the binding of BOFP to all six Gram-positive FtsZ proteins at 25° C. (1.02±0.09 to 3.49±0.25 µM) indicates a much broader spectrum of FtsZ targeting as well as a binding affinity that is approximately 3- to 29-fold higher.

Figures 6A, 6B, 6C, 6D, 6E, 6F, 6G, 6H, 6I, 6J, 6K, 6L:
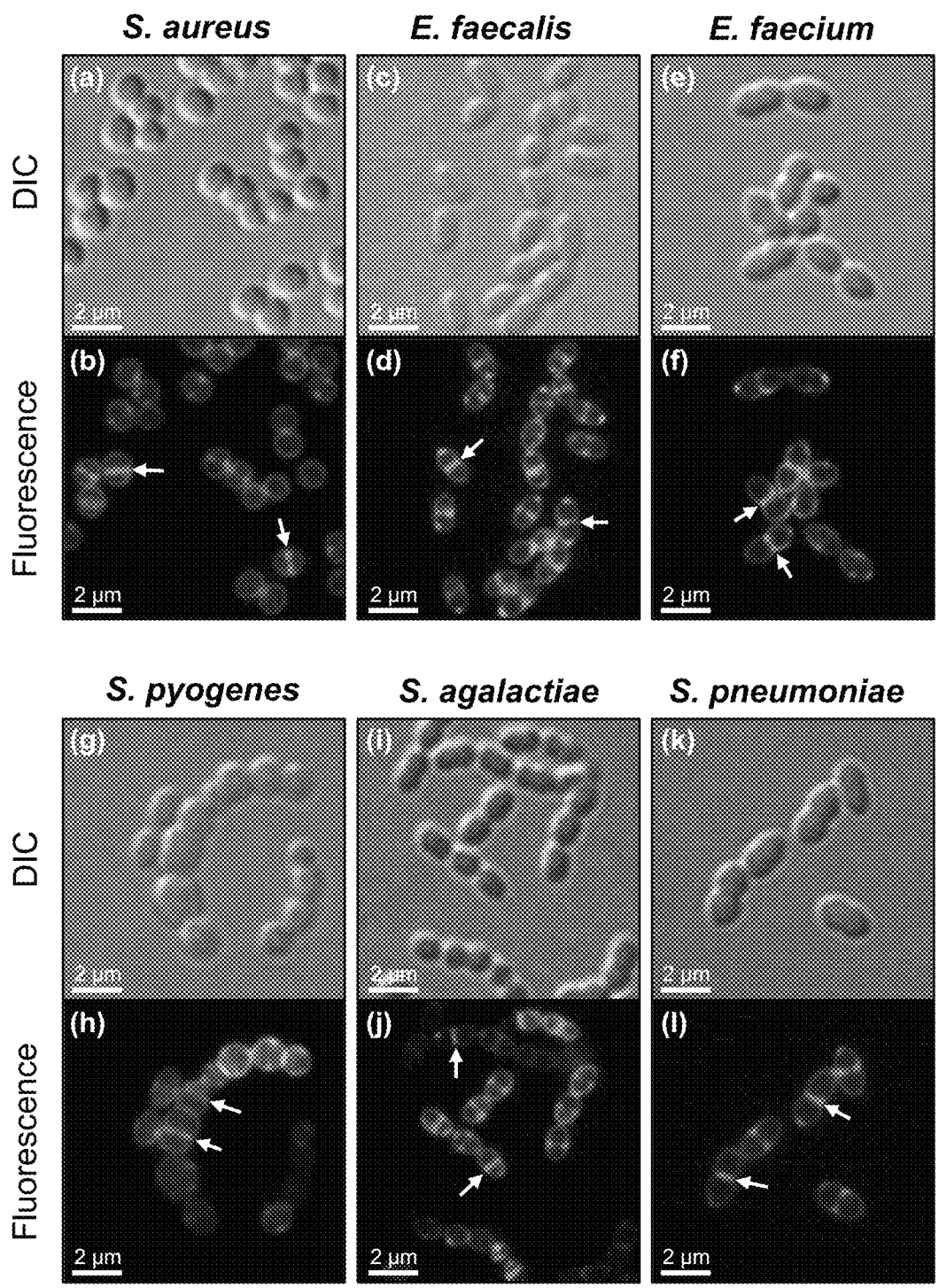
FIGS. 6A-6L: FtsZ visualization in the Gram-positive bacterial pathogens *S. aureus* NRS705 (FIGS. 6a,b), *E. faecalis* ATCC 29212 (FIGS. 6c,d), *E. faecium* ATCC 19434 (FIGS. 6e,f), *S. pyogenes* ATCC 19615 (FIGS. 6g,h), *S. agalactiae* ATCC 12386 (FIGS. 6i,j), and *S. pneumonieae* ATCC 49619 (FIGS. 6k,l). Differential interference contrast (DIC) and fluorescence micrographs of the indicated bacterial cells treated for 5 minutes with 1 μg/mL BOFP just prior to visualization. The arrows in 6b, 6d, 6f, 6h, 6j, and 6l highlight representative FtsZ Z-rings at midcell labeled by BOFP.
Figures 7A, 7B, 7C, 7D, 7E:
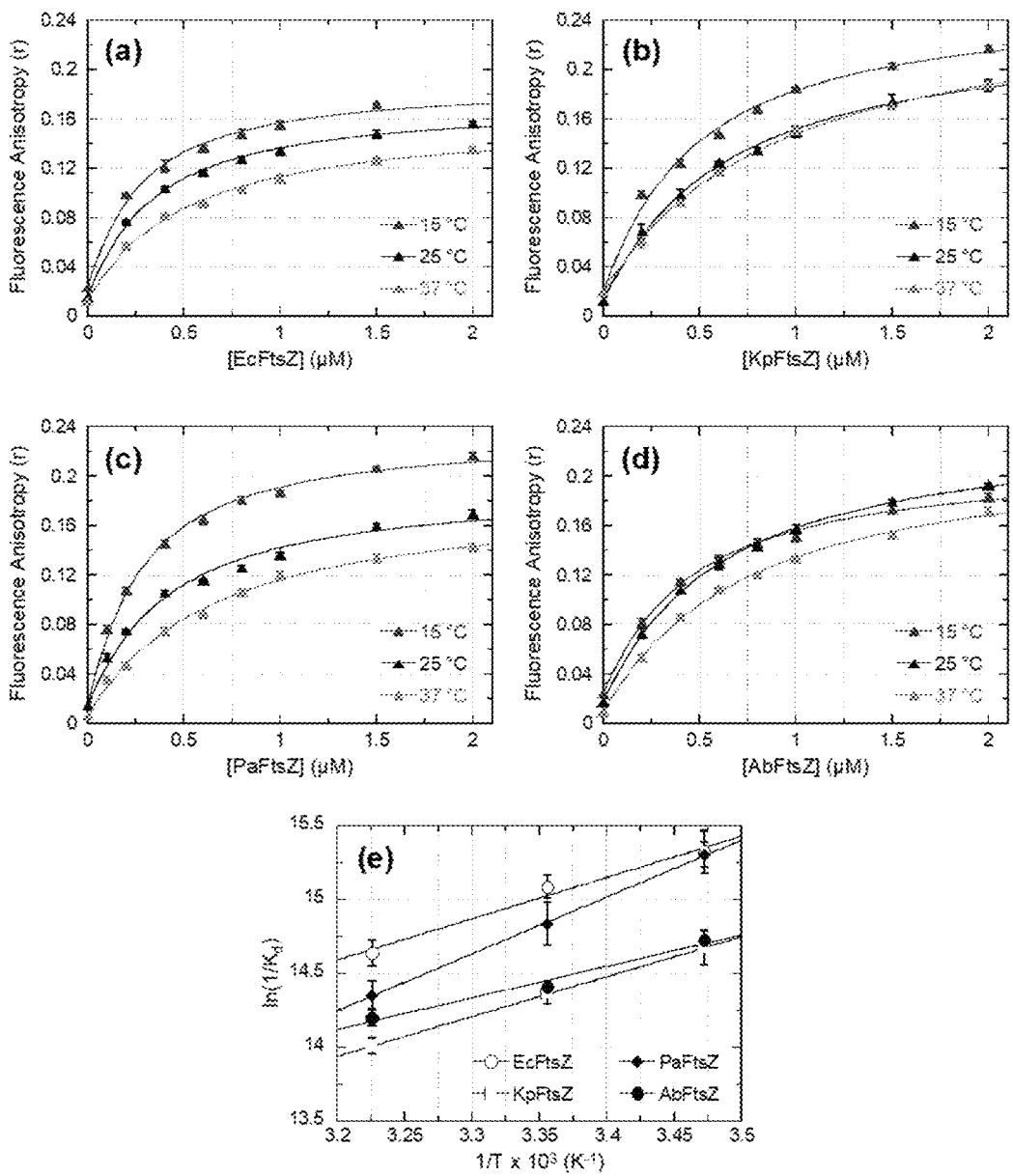
FIGS. 7A-7E: Fluorescence anisotropy profiles of 0.1 μM BOFP as a function of increasing concentrations of *Escherichia coli* FtsZ (EcFtsZ) (FIG. 7a), *Klebsiella pneumoniae* FtsZ (KpFtsZ) (FIG. 7b), *Pseudomonas aeruginosa* FtsZ (PaFtsZ) (FIG. 7c), or *Acinetobacter baumannii* FtsZ (AbFtsZ) (FIG. 7d). Acquisition and display parameters are as described in the legend to FIG. 3. Panel (FIG. 7e) shows plots of $\ln(1/K_d)$ vs. 1/T for the interaction of BOFP with EcFtsZ (open circles), KpFtsZ (open squares), PaFtsZ (filled diamonds), and AbFtsZ (filled circles). The solid lines reflect linear fits of the experimental data points with Eq. 3.

Brief exposure to a low concentration of BOFP effectively labels FtsZ in live *S. aureus*, *E. faecalis*, *E. faecium*, *S. pyogenes*, *S. agalactiae*, and *S. pneumoniae* cells. Having demonstrated the high-affinity binding of BOFP to the Gram-positive FtsZ proteins SaFtsZ, EfsFtsZ, EfmFtsZ, SpyFtsZ, SagFtsZ, and SpnFtsZ, the potential of the probe to label FtsZ in live cells from the corresponding pathogens themselves was investigated. FIG. 6 shows differential interference contrast (DIC) and fluorescence micrographs of *S. aureus*, *E. faecalis*, *E. faecium*, *S. pyogenes*, *S. agalactiae*, and *S. pneumoniae* cells labeled for 5 minutes with 1 µg/mL (1.3 µM) BOFP were generated. In each of the six pathogens, bright bands of fluorescence staining were clearly visible at midcell (as highlighted by the arrows in FIGS. 6b, 6d, 6f, 6h, 6j, and 6l), consistent with the labeling of FtsZ Z-rings formed in the process of cell division. Additional fluorescence staining (though weaker than that at midcell) was also evident along the periphery of each cell, suggesting that FtsZ is also localized throughout the cell membrane. These results indicate that brief exposure to a low concentration of BOFP affords outstanding visualization of FtsZ and its localization patterns in live Gram-positive bacterial cells.

BOFP targets FtsZ proteins from Gram-negative bacterial pathogens with an even higher affinity than FtsZ proteins from Gram-positive pathogens. In addition to targeting Gram-positive FtsZ proteins, the ability of BOFP to target Gram-negative FtsZ proteins was also investigated. Fluorescence anisotropy was used to explore the interactions of BOFP with the FtsZ proteins from the four Gram-negative pathogens, *E. coli* (EcFtsZ), *K. pneumoniae* (KpFtsZ), *P. aeruginosa* (PaFtsZ), and *A. baumannii* (AbFtsZ), with the resulting anisotropy profiles acquired at 15, 25, and 37° C. being depicted in FIGS. 7a-7d. Inspection and analysis of these anisotropy profiles reveals that BOFP binds to all four Gram-negative FtsZ proteins with sub-micromolar affinity. At 25° C., the $K_d$ values for EcFtsZ, KpFtsZ, PaFtsZ, and AbFtsZ are 0.28±0.02, 0.58±0.04, 0.36±0.06, and 0.55±0.02 µM, respectively (Table 1). A comparison of the $K_d$ values at 25° C. listed in Table 1 indicates that BOFP binds the Gram-negative FtsZ proteins with an approximately 2- to 12-fold higher affinity than the Gram-positive FtsZ proteins. Thus, in striking contrast to the early-generation fluorescent FtsZ inhibitors reported by Artola, M. et al., *Chem. Sci.* 8, 1525-1534 (2017), BOFP can target a broad range Gram-negative FtsZ proteins with a high degree of affinity.

For the majority of target FtsZ proteins studied, enthalpy provides a significant driving force for the binding of BOFP. The temperature dependence of the $K_d$ values for the binding of BOFP to the Gram-positive and Gram-negative FtsZ proteins was used to derive the thermodynamic parameters associated with the binding reactions. Free energy changes (ΔG) at 37° C. (310 K) were derived from the corresponding $K_d$ values using Eq. 2, while enthalpy and entropy changes (ΔH and ΔS, respectively) were determined from linear fits of the $\ln(1/K_d)$ vs. 1/T plots shown in FIGS. 5f and 7e with Eq. 3. The resulting thermodynamic parameters are listed in Table 1. For seven of the ten FtsZ proteins studied (SaFtsZ, EfsFtsZ, SpyFtsZ, SagFtsZ, EcFtsZ, KpFtsZ, and PaFtsZ), ΔH contributes >50% to the observed ΔG ΔG of binding, with the enthalpic contribution to binding being 100% for two of those seven FtsZ proteins (SaFtsZ and EfsFtsZ). These favorable enthalpic contributions to binding likely stem from the extensive array of favorable van der Waals contacts between the host protein and both the 1 and BODIPY portions of the probe. For the remaining three FtsZ proteins (EfmFtsZ, SpnFtsZ, and AbFtsZ), ΔS contributes >50% to the observed ΔG of binding. These favorable entropic contributions to binding may reflect favorable binding-induced changes in hydration and/or conformation of the host proteins.

Figures 8A, 8B, 8C, 8D, 8E, 8F, 8G, 8H:
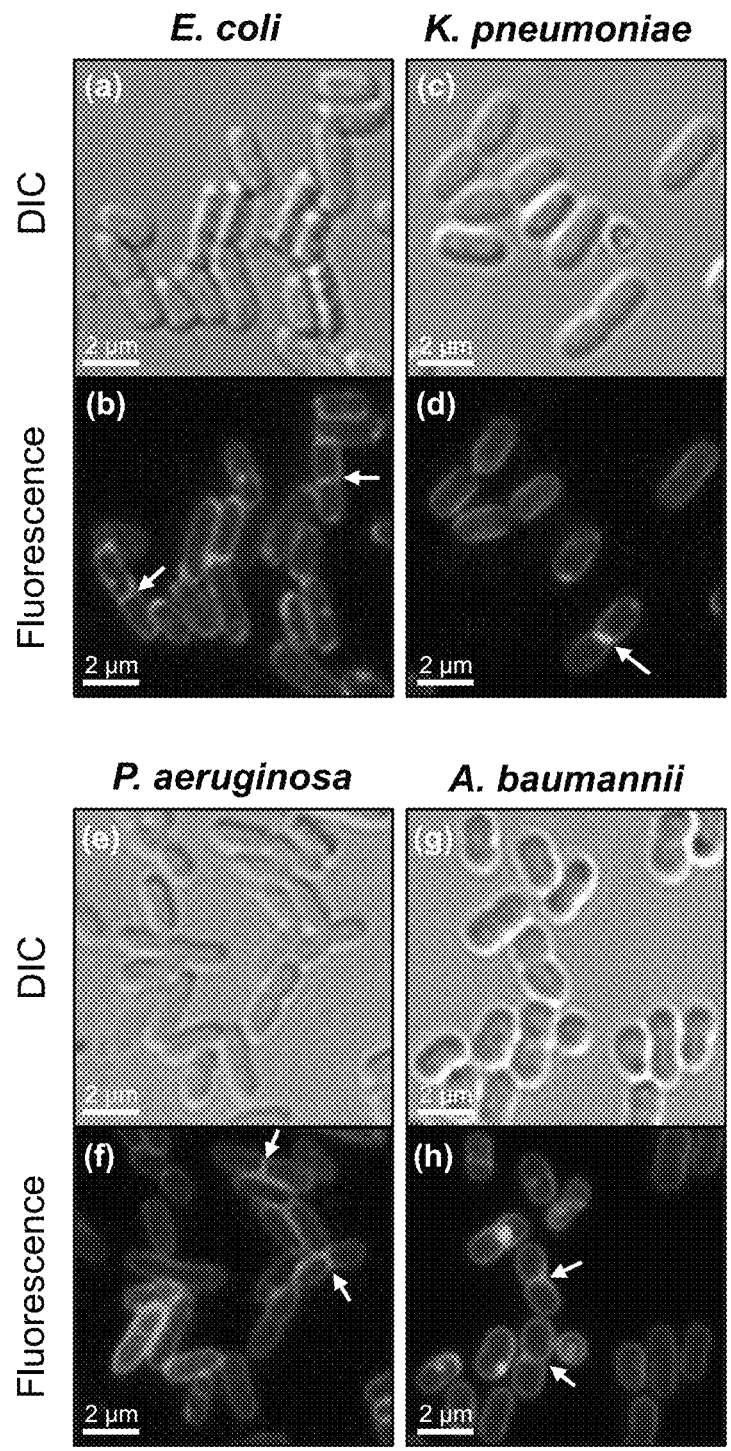
FIGS. 8A-8H: FtsZ visualization in the Gram-negative bacterial pathogens *E. coli* ATCC 25922 (FIGS. 8a-b), *K. pneumoniae* ATCC 13883 (FIGS. 8c-d), *P. aeruginosa* ATCC 27853 (FIGS. 8e-f), and *A. baumannii* ATCC 19606 (FIGS. 8g-h). Differential interference contrast (DIC) and fluorescence micrographs of the indicated bacterial cells treated for 5 min with 1 μg/mL BOFP in the presence of pentamidine isethionate (at 0.875 mg/mL for *E. coli* and 3.5 mg/mL for the other three strains) just prior to visualization. The arrows in 8b, 8d, 8f, and 8h highlight representative FtsZ Z-rings at midcell labeled by BOFP.

In addition to Gram-positive bacterial cells, BOFP also labels FtsZ effectively in live *E. coli*, *K. pneumoniae*, *P. aeruginosa*, and *A. baumannii* cells. The potential of the probe to label FtsZ in live Gram-negative bacterial cells was investigated. When exposed to BOFP in a similar manner (1 µg/mL for 5 minutes) to that described above for the Gram-positive bacteria, little or no FtsZ labeling in the Gram-negative cells was observable by fluorescence. Previous studies have indicated that the large size of fluorescent antibiotics resulting from the conjugation of bulky fluorophores restricts the passage of the agents across the outer membrane of Gram-negative cells (Matijašić, M. et al., *Pharmacol. Res.* 66, 332-342 (2012)). Stokes, J. M. et al, *Nat. Microbiol.* 2, 17028 (2017) have shown that pentamidine can effectively permeabilize the outer membrane of Gram-negative bacterial cells to large antibiotics that would normally be unable to cross the membrane. When co-treating *K. pneumoniae* cells with 1 µg/mL BOFP and 3.5 mg/mL pentamidine isethionate for 5 minutes, bright fluorescence staining is visible both at midcell and along the cell periphery (FIG. 8b). Co-treatment of *E. coli*, *P. aeruginosa*, and *A. baumannii* cells results in a similar fluorescence staining pattern to that observed in *K. pneumoniae* cells (FIGS. 8b, 8d, 8f, and 8h). The fluorescent bands visible at midcell were consistent with the labeling of FtsZ Z-rings during the process of cell division, with the peripheral staining reflecting the presence of FtsZ in the cell membrane as well. Viewed as a whole, these results indicate that BOFP is useful for visualizing FtsZ not only in live Gram-positive cells, but also in live Gram-negative cells.

BOFP can also be used to visualize the impact of non-fluorescent FtsZ inhibitors on the localization of FtsZ in both Gram-positive and Gram-negative bacterial cells. For BOFP to be useful as a tool for identifying new FtsZ inhibitors in a live cell-based assay, it should facilitate the detection of changes in FtsZ localization induced by other test compounds with the potential for FtsZ inhibition. Toward this end, the ability of BOFP to visualize the impact of the oxazole-benzamide inhibitor 1 on FtsZ localization in live *S. aureus*, *E. coli*, and *K. pneumoniae* cells was investigated. As expected with a known FtsZ inhibitor, treatment with 1 induced a significant change in cell morphology consistent the impairment of cell division (FIG. 9). This morphological change takes the form of cell enlargement in cocci like *S. aureus* (FIG. 9g) and filamentation in rods like *E. coli* and *K. pneumoniae* (FIGS. 9i and 9k) Significantly, BOFP effectively labeled FtsZ in the 1-treated cells, showing clear mislocalization of FtsZ and an absence of Z-rings in any of the treated cells (FIGS. 9h, 9j, and 9l). In addition, the presence of FtsZ in the membrane of 1-treated cells is reduced relative to that in untreated cells. In *S. aureus*, similar results were observed for cells treated with the benzamide FtsZ inhibitors PC190723 and TXA707. These collective results highlight the usefulness of BOFP as a screening tool for identifying novel FtsZ inhibitors in both Gram-positive and Gram-negative pathogens. The fluorescent FtsZ inhibitors previously reported by Artola et al. lacked this utility, as their ability to label FtsZ was significantly diminished in live cells treated with known FtsZ inhibitors like PC190723 (Artola, M. et al., *Chem. Sci.* 8, 1525-1534 (2017)).

Conclusions

A fluorescent FtsZ-targeting probe (BOFP) was prepared. Fluorescence anisotropy studies with BOFP provide the first demonstration of a fluorescent probe capable of targeting the FtsZ proteins from a broad range of clinically relevant Gram-positive and Gram-negative bacterial pathogens with a high degree of affinity. In addition, fluorescence microscopy studies highlight the utility of BOFP for visualizing FtsZ and monitoring cell division in these pathogenic bacteria as well as for visualizing the impact of inhibitors on FtsZ localization. These properties make BOFP a robust tool for identifying new broad-spectrum FtsZ inhibitors and delineating their mechanisms of action.

Methods

Fluorescence anisotropy assay for determining the affinities and thermodynamics associated with the binding of BOFP to FtsZ proteins. Fluorescence anisotropy experiments were performed using an AVIV model ATF105 spectrofluorometer at 15, 25, or 37° C. In these experiments, bandwidths were set to 4 nm in both the excitation and emission directions, with the excitation and emission wavelengths being set at 488 nm and 510 nm, respectively. BOFP (0.1 µM) was titrated with increasing concentrations (ranging from 0 to 12 µM) of FtsZ in 120 µL of buffer containing 50 mM Tris-HCl (pH 7.6) and 50 mM KCl. After each protein addition, the samples were equilibrated for 3 minutes, whereupon the fluorescence anisotropy was measured.

Figure 3:
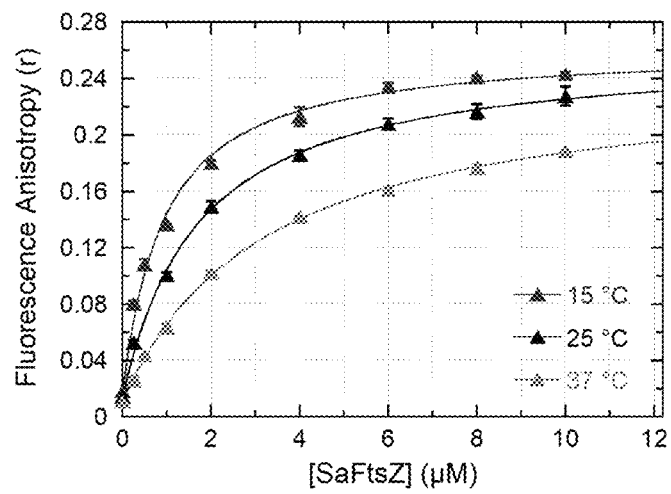
FIG. 3: Fluorescence anisotropy profiles of 0.1 μM BOFP as a function of increasing concentrations of *S. aureus* FtsZ (SaFtsZ). The titration experiments were conducted at 15° C., 25° C., or 37° C. in solution containing 50 mM Tris-HCl (pH 7.6) and 50 mM KCl. The solid lines reflect non-linear least squares fits of the experimental data points with Eq. 1.
Figure 4:
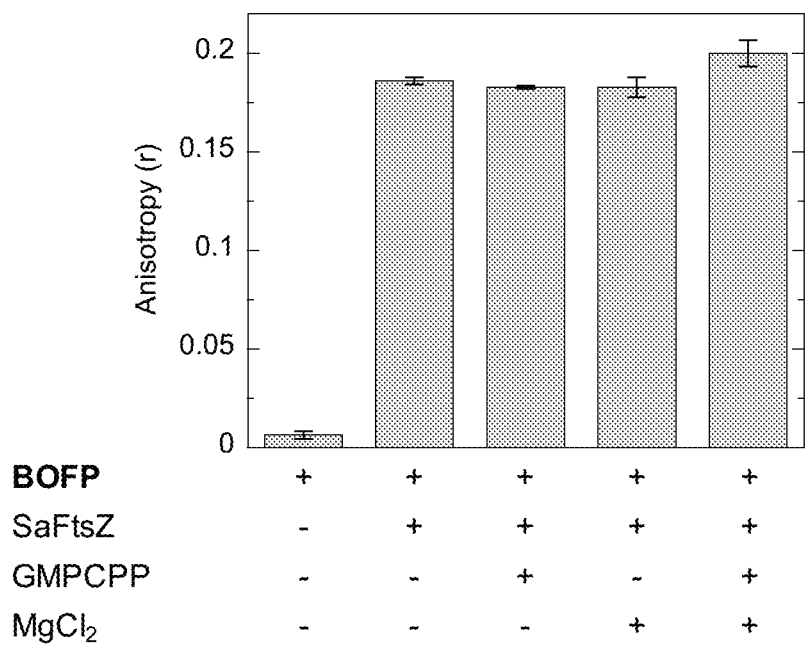
FIG. 4. Fluorescence anisotropy of BOFP (0.1 μM) alone or in complex with SaFtsZ (10 μM), with the latter also being shown in the presence of GMPCPP (0.1 mM), $MgCl_2$ (10 mM), or both. Anisotropy measurements were conducted at 37° C. in solution containing 50 mM Tris-HCl (pH 7.6) and 50 mM KCl.

Plots of the fluorescence anisotropy (r) of BOFP as a function of FtsZ concentration (as shown in FIGS. 3, 5, and 7) were analyzed by non-linear least squares regression using the following 1:1 binding formalism:

$$r = r_0 + \frac{r_\infty - r_0}{2[C]_{tot}} \left[ ([C]_{tot} + [P]_{tot} + K_d) - \sqrt{([C]_{tot} + [P]_{tot} + K_d)^2 - 4[C]_{tot}[P]_{tot}} \right] \quad \text{(Eq. 1)}$$

In this equation, $r_0$ is the anisotropy of the protein-free compound, $r_\infty$ is the anisotropy of the compound in the presence of an infinite concentration of FtsZ, $[C]_{tot}$ is the total concentration of the compound, and $[P]_{tot}$ is the total concentration of protein with each addition. These analyses yielded the equilibrium dissociation constant ($K_d$) for each binding reaction.

The binding free energy ($\Delta G$) at temperature T was derived from the corresponding $K_d$ value determined at T using the following relationship:

$$\Delta G = -RT \ln\left(\frac{1}{K_d}\right) \quad \text{(Eq. 2)}$$

Figures 5A, 5B, 5C, 5D, 5E, 5F:
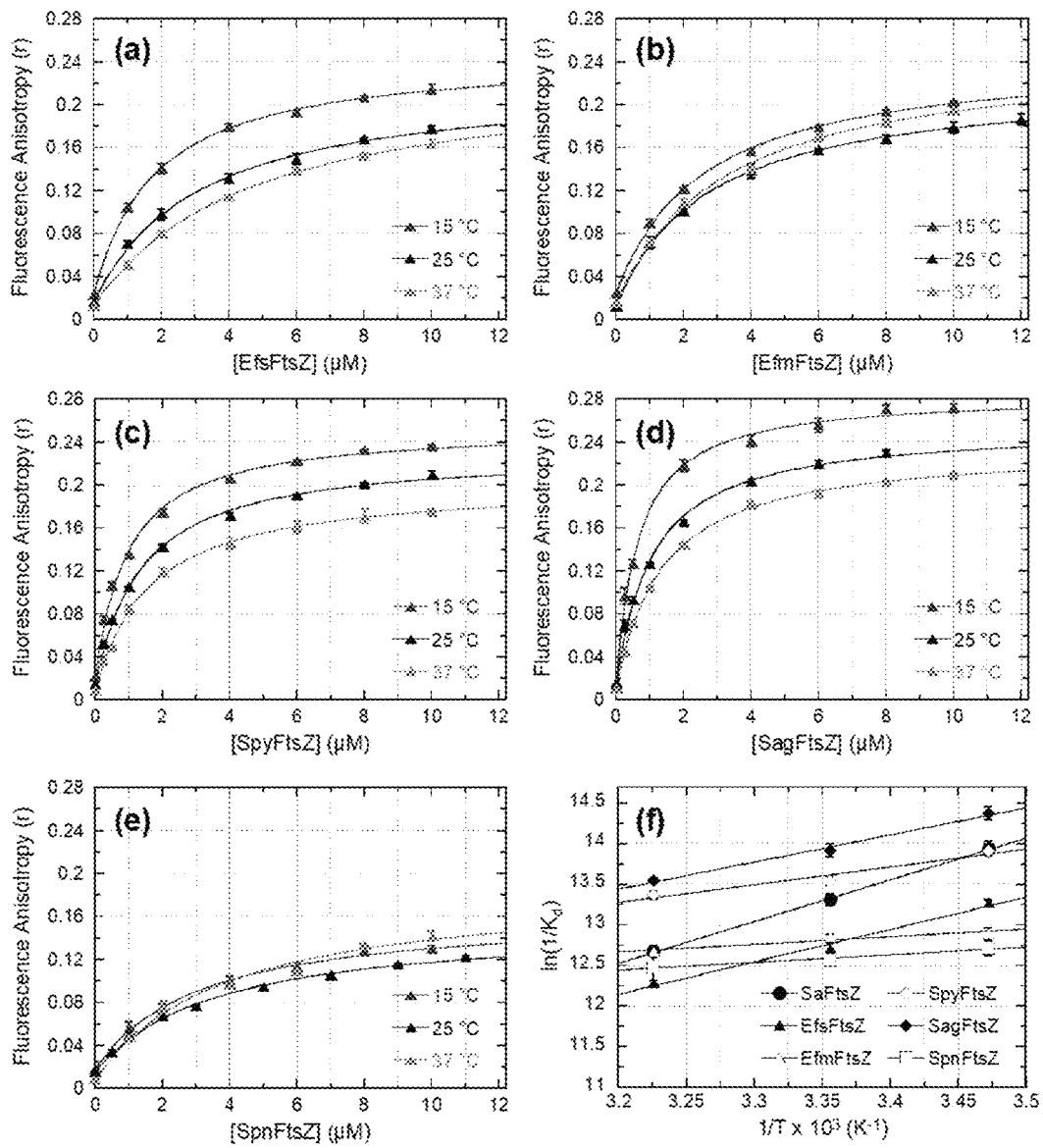
FIGS. 5A-5F: Fluorescence anisotropy profiles of 0.1 μM BOFP as a function of increasing concentrations of *Enterococcus faecalis* FtsZ (EfsFtsZ) (FIG. 5a), *Enterococcus faecium* FtsZ (EfmFtsZ) (FIG. 5b), *Streptococcus pyogenes* FtsZ (SpyFtsZ) (FIG. 5c), *Streptococcus agalactiae* FtsZ (SagFtsZ) (FIG. 5d), or *Streptococcus pneumoniae* FtsZ (SpnFtsZ) (FIG. 5e). Acquisition and display parameters are as described in the legend to FIG. 3. Panel (FIG. 5f) shows plots of $\ln(1/K_d)$ vs. 1/T for the interaction of BOFP with SaFtsZ (filled circles), EfsFtsZ (filled triangles), EfmFtsZ (open triangles), SpyFtsZ (open diamonds), SagFtsZ (filled diamonds), and SpnFtsZ (open squares). The solid lines reflect linear fits of the experimental data points with Eq. 3.

The binding enthalpy ($\Delta H$) and entropy ($\Delta S$) were derived from linear fits of the $\ln(1/K_d)$ vs. $1/T$ plots shown in FIGS. 3f and 5e using the following relationship:

$$\ln\left(\frac{1}{K_d}\right) = -\frac{\Delta H}{R}\left(\frac{1}{T}\right) + \frac{\Delta S}{R} \quad \text{(Eq. 3)}$$

A quartz ultra-micro cell (Hellma) with a 2×5 mm aperture and a 15 mm center height was used for all measurements. The pathlengths in the excitation and emissions directions were 1 and 0.2 cm, respectively. All steady-state anisotropy experiments were conducted in at least triplicate, with the reported anisotropies reflecting the average values.

Fluorescence microscopy assay for visualizing FtsZ and monitoring cell division in live Gram-positive and Gram-negative bacterial cells using BOFP. All fluorescence microscopy experiments were conducted using an Olympus BX50 microscope equipped with an X-cite Exacte 200W mercury lamp, a 100× Olympus UPLSAPO oil immersion objective (1.40 aperture), and a Chroma ET-EGFP (FITC/Cy2) filter. Images were captured using a QImaging Retiga R3 charge-coupled device (CCD) camera and the Ocular-Version 2.0 software package (QImaging).

For visualizing FtsZ in Gram-positive bacteria using BOFP, the bacterial cells were grown to log-phase in media suitable for each individual pathogen. Specifically, *S. aureus* NRS705 was grown in tryptic soy broth (TSB), *E. faecalis* ATCC 29212 and *E. faecium* ATCC 19434 were grown in lactobacilli MRS broth, *S. agalactiae* ATCC 12386 and *S. pneumoniae* ATCC 49619 were grown in TH broth, and *S. pyogenes* ATCC 19615 was grown in CAMH broth supplemented with 3% (v/v) LHB. For each Gram-positive bacterial strain, a total of 1 mL of cell culture was centrifuged at 15,000×g for 1 minute and washed 2-3 times with 1 mL of PBS. After the final wash, the pelleted cells were resuspended in 500 μL of PBS containing 1 μg/mL of BOFP and incubated in the dark for 5 minutes at room temperature. The cells were then centrifuged at 15,000×g for 1 minute, washed twice with 1 mL of PBS, and subsequently resuspended in 200 μL of PBS. 8 μL of this final cell suspension was then spread on a 0.25 mm layer of 1.5% high-resolution agarose (Sigma) in PBS, which was mounted on a standard 75×25×1 mm microscope slide (Azer Scientific) using a 1.7×2.8×0.025 cm Gene Frame (ThermoFisher). A 24×40 mm cover slip (Azer Scientific) was then applied to the agarose pad to prepare the slide for microscopic visualization.

For visualizing FtsZ in Gram-negative bacteria using BOFP, *E. coli* ATCC 25922, *K. pneumoniae* ATCC 13883, *P. aeruginosa* ATCC 27853, and *A. baumannii* ATCC 19606 were grown to log-phase in CAMH broth. For each Gram-negative bacterial strain, a total of 1 mL of cell culture was centrifuged at 15,000×g for 1 minute and washed twice with 1 mL of Tris-buffered saline (TBS) composed of 50 mM Tris-HCl pH 7.6 and 150 mM NaCl. After the final wash, the pelleted cells were resuspended in 500 μL of TBS containing 1 μg/mL of BOFP and pentamidine isethionate (at 0.875 mg/mL for *E. coli* and 3.5 mg/mL for the other three strains). The resuspended cells were then incubated in the dark for 5 minutes at room temperature, centrifuged at 15,000×g for 1 minute, washed twice with 1 mL of TBS, and subsequently resuspended in 200 μL of TBS. This final cell suspension was then prepared for microscopy as described above for the Gram-positive bacterial strains.

Fluorescence microscopy assay for visualizing the impact of FtsZ inhibitors in live Gram-positive and Gram-negative bacterial cells using BOFP. To visualize the impact of treatment with the oxazole-benzamide FtsZ inhibitor 1 using BOFP, *S. aureus* NRS705, *E. coli* N43, and *K. pneumoniae* ATCC 10031 were grown to log-phase in CAMH broth and diluted to an $OD_{600}$ of 0.1. Each cell culture was then treated with either DMSO vehicle or 1 at 4×MIC (2 μg/mL for *S. aureus* or 4 μg/mL for *E. coli* and *K. pneumoniae*) for 3 hours at 37° C. Following this treatment, 1 mL of each culture was centrifuged at 15,000×g for 1 minute and washed twice with 1 mL of PBS (for *S. aureus*) or TBS (for *E. coli* and *K. pneumoniae*). The resulting *S. aureus* cell pellets were further processed as described above for the Gram-positive bacterial strains and the resulting *E. coli* and *K. pneumoniae* cell pellets were further processed as described above for the Gram-negative bacterial strains. The impact of treatment with the benzamide FtsZ inhibitors PC190723 and TXA707 at 4×MIC (2 μg/mL for PC190723 or 4 μg/mL for TXA707) was also examined in *S. aureus* NRS705 cells as described above.

Example 2. Synthesis of BOFP

As schematically depicted in FIG. 2, 2-(5-bromo-4-(4-(trifluoromethyl)phenyl)-oxazol-2-yl)-2-(3-carbamoyl-2,4-difluorophenoxy)ethyl 3-(5,5-difluoro-7,9-dimethyl-5H-5λ⁴,6λ⁴-dipyrrolo[1,2-c:2',1'-f][1,3,2]diazaborinin-3-yl) propanoate (BOFP) was synthesized by adding BODIPY FL-COOH (12 mg, 0.04 mmol), 1-ethyl-3-(3-dimethylaminopropyl)-carbodiimide (EDC) (12 mg, 0.06 mmol), and 4-dimethylaminopyridine (DMAP) (5.0 mg, 0.04 mmol) to 2 (20 mg, 0.04 mmol) in $CH_2Cl_2$ (3 mL). The reaction mixture was stirred at room temperature overnight. The reaction mixture was diluted with $CH_2Cl_2$ and washed with brine. The organic layer was dried over sodium sulfate and filtered. The filtrate was concentrated and purified using ISCO column chromatography on silica gel (50% ethyl acetate/hexanes) to give the product (25 mg, 82% yield) as a deep red solid. $^1$H NMR (300 MHz, CDCl$_3$) δ 8.06 (d, J=8.41 Hz, 1H), 7.68 (d, J=9.0 Hz, 1H), 7.19 (m, 1H), 6.83 (m, 1H), 6.81 (d, J=3.9 Hz, 1H), 6.23 (d, J=3.9 Hz, 1H), 6.11 (s, 2H), 5.86 (s, 2H), 5.42 (dd, J=4.8, 7.8 Hz, 1H), 4.81 (dd, J=7.8, 11.4 Hz, 1H), 4.67 (dd, J=4.8, 11.7 Hz, 1H), 3.27 (t, J=7.8 Hz, 1H), 2.81 (t, J=7.5 Hz, 1H), 2.53 (s, 3H), 2.24 (s, 3H). Electrospray ionization (ESI) high-resolution mass spectrometry (HRMS) of BODIPY dyes typically yields [M+H-HF]$^+$ as the most abundant product ion, due to neutral loss of HF (Qi, Y., et al., Rapid Commun. Mass Spectrom. 29, 885-890 (2015)). [M+H-HF]$^+$ was observed as the most abundant ion of our reaction product, with the ESI HRMS of $C_{33}H_{25}BBrF_7N_4O_5$ being: [M+H-HF]$^+$ calculated 762.2899, found 762.1049.

Representative probes of the invention overcome one or more of the limitations associated with earlier-generation probes. Fluorescence anisotropy studies demonstrate that BOFP can target the FtsZ proteins from a broad range of Gram-positive pathogens (including *S. aureus, Enterococcus faecalis, Enterococcus faecium, Streptococcus pyogenes, Streptococcus agalactiae,* and *Streptococcus pneumoniae*) with high affinity ($K_d$ values in the range of 1.0 to 3.5 µM at 25° C.). Significantly, BOFP targets the FtsZ proteins from clinically important Gram-negative pathogens (including *E. coli, Klebsiella pneumoniae, Pseudomonas aeruginosa,* and *Acinetobacter baumannii*) with an even higher affinity ($K_d$ values in the range of 0.22 to 0.82 µM). Most importantly, fluorescence microscopy studies demonstrate that brief exposure to BOFP (at a concentration of only 1.3 µM) can be used to visualize FtsZ in all the Gram-positive and Gram-negative bacterial pathogens listed above, even when pre-treated with other FtsZ inhibitors. Taken together, these results indicate that BOFP can serve as a powerful tool for identifying new broad-spectrum FtsZ inhibitors as well as their mechanisms of action.

Fluorescent analogs centered on the benzamide inhibitor PC190723 bind FtsZ from the Gram-positive bacteria *Staphylococcus aureus* and *Bacillus subtilis*. However, these interactions are weak (with estimated $K_d$ values in the range of 11 to 29 µM for FtsZ from *Bacillus subtilis* at 25° C.). The fluorescent analogs centered on PC190723 were not shown to interact with the FtsZ proteins from any other Gram-positive bacterial pathogens.

Fluorescence anisotropy studies reveal that BOFP can target the FtsZ proteins from a much broader range of clinically significant Gram-positive bacterial pathogens (including *Staphylococcus aureus, Enterococcus faecalis, Enterococcus faecium, Streptococcus pyogenes, Streptococcus agalactiae,* and *Streptococcus pneumoniae*) with higher affinity ($K_d$ values in the range of 1.0 to 3.5 µM at 25° C.). The lower range of $K_d$ values we observe for the binding of BOFP to all six Gram-positive FtsZ proteins at 25° C. indicates a much broader spectrum of FtsZ targeting activity as well as a binding affinity that is approximately 3- to 29-fold higher.

The fluorescent analogs of the benzamide FtsZ inhibitor PC190723 required both GTP and magnesium in order to bind FtsZ from *Staphylococcus aureus*.

The binding of BOFP to FtsZ from *Staphylococcus aureus* is independent of either GTP or magnesium.

None of the analogs of the benzamide FtsZ inhibitor PC190723 were able to bind FtsZ from the Gram-negative bacterium *Escherichia coli* to a significant degree.

BOFP can target not only the FtsZ proteins from a broad range of Gram-positive bacterial pathogens, but also the FtsZ proteins from clinically important Gram-negative pathogens (including *Escherichia coli, Klebsiella pneumoniae, Pseudomonas aeruginosa,* and *Acinetobacter baumannii*). Significantly, BOFP targets the Gram-negative FtsZ proteins with an even higher affinity ($K_d$ values in the range of 0.22 to 0.82 µM) than the Gram-positive FtsZ proteins.

One fluorescent analog of the benzamide inhibitor PC190723 was used to visualize FtsZ in the Gram-positive bacteria *Staphylococcus aureus* and *Bacillus subtilis*. However, visualization required prolonged treatment with large concentrations of the analog (25 to 200 µM) and was lost upon pre-treatment with the parent inhibitor PC190723, further limiting the usefulness of the analog as a screening tool for FtsZ inhibitors. Visualization of FtsZ in no other Gram-positive or Gram-negative bacteria was demonstrated for this fluorescent analog of PC190723.

Fluorescence microscopy studies demonstrate that brief exposure to BOFP (at a concentration of only 1.3 µM) can be used to visualize FtsZ and monitor cell division in live cells from all the Gram-positive and Gram-negative bacterial pathogens noted above, even when the cells were pre-treated with other FtsZ inhibitors.

In the area of marine and aquatic microbiology, a method is provided to detect, identify, or monitor cell division in marine and aquatic bacteria, including bacteria of the phylum Bacteroidetes.

In the area of skin and gut microbiomes, a method is provided to detect, identify, or monitor cell division in skin and gut bacteria, including bacteria of the phyla Firmicutes and Bacteroidetes, Actinobacteria, and Proteobacteria.

In the area of food microbiology, a method is provided to detect, identify, or monitor cell division in the main types of bacteria found in food, including *Campylobacter, Clostridium perfringens, Escherichia coli, Salmonella,* and *Listeria*.

TABLE 1

Equilibrium affinity constants and thermodynamic parameters for the binding of BOFP to FtsZ proteins from Gram-positive and Gram-negative bacteria.

| FtsZ Protein | $^a K_d$ –15° C. [µM] | $^a K_d$ –25° C. [µM] | $^a K_d$ –37° C. [µM] | $^b \Delta H$ [kcal/mol] | $^b \Delta S$ [cal/mol · K] | $^c \Delta G$ [kcal/mol] |
|---|---|---|---|---|---|---|
| Gram-Positive: | | | | | | |
| S. aureus (SaFtsZ) | 0.88 ± 0.08 | 1.66 ± 0.12 | 3.14 ± 0.13 | −10.2 ± 0.3 | −7.8 ± 1.0 | −7.8 ± 0.1 |
| E. faecalis (EfsFtsZ) | 1.72 ± 0.06 | 3.05 ± 0.25 | 4.62 ± 0.12 | −7.9 ± 1.0 | −1.2 ± 3.3 | −7.6 ± 0.1 |
| E. faecium (EfmFtsZ) | 2.50 ± 0.14 | 2.62 ± 0.08 | 3.14 ± 0.22 | −1.9 ± 0.6 | +19.2 ± 1.9 | −7.8 ± 0.1 |
| S. pyogenes (SpyFtsZ) | 0.91 ± 0.06 | 1.31 ± 0.08 | 1.55 ± 0.08 | −4.3 ± 1.1 | +12.8 ± 3.7 | −8.2 ± 0.1 |
| S. agalactiae (SagFtsZ) | 0.62 ± 0.05 | 1.02 ± 0.09 | 1.31 ± 0.04 | −6.6 ± 0.6 | +5.4 ± 2.0 | −8.2 ± 0.1 |
| S. pneumoniae (SpnFtsZ) | 3.02 ± 0.30 | 3.49 ± 0.25 | 3.81 ± 0.69 | −1.9 ± 0.3 | +18.7 ± 1.2 | −7.7 ± 0.1 |

TABLE 1-continued

Equilibrium affinity constants and thermodynamic parameters for the binding of BOFP to FtsZ proteins from Gram-positive and Gram-negative bacteria.

| FtsZ Protein | [a]$K_d$ –15° C. [μM] | [a]$K_d$ –25° C. [μM] | [a]$K_d$ –37° C. [μM] | [b]$\Delta H$ [kcal/mol] | [b]$\Delta S$ [cal/mol · K] | [c]$\Delta G$ [kcal/mol] |
|---|---|---|---|---|---|---|
| Gram-Negative: | | | | | | |
| *E. coli* (EcFtsZ) | 0.22 ± 0.03 | 0.28 ± 0.02 | 0.44 ± 0.04 | −5.6 ± 0.8 | +11.2 ± 2.7 | −9.0 ± 0.1 |
| *K. pneumoniae* (KpFtsZ) | 0.42 ± 0.05 | 0.58 ± 0.04 | 0.82 ± 0.04 | −5.4 ± 0.1 | +10.5 ± 0.1 | −8.6 ± 0.1 |
| *P. aeruginosa* (PaFtsZ) | 0.23 ± 0.02 | 0.36 ± 0.06 | 0.58 ± 0.06 | −7.7 ± 0.2 | +3.8 + 0.6 | −8.8 ± 0.1 |
| *A. baumannii* (AbFtsZ) | 0.40 ± 0.03 | 0.55 ± 0.02 | 0.68 ± 0.04 | −4.2 ± 0.6 | +14.5 ± 2.1 | −8.8 ± 0.1 |

[a]$K_d$ values (determined at 15, 25, and 37° C.) were derived from non-linear least squares fits of the fluorescence anisotropy profiles shown in FIGS. 3, 5, and 7 with Eq. 1, with the indicated uncertainties reflecting the standard deviation of the fitted curves from the experimental data points.
[b]$\Delta H$ and $\Delta S$ values were derived from linear fits of the ln(1/$K_d$) vs. 1/T plots shown in FIGS. 5 and 6 with Eq. 3, with the indicated uncertainties reflecting the standard deviation of the fitted lines from the experimental data points.
[c]$\Delta G$ values were calculated at T = 310K (37° C.) using Eq. 2 and the corresponding values of $K_d$, with the indicated uncertainties reflecting the maximal errors as propagated through that equation.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

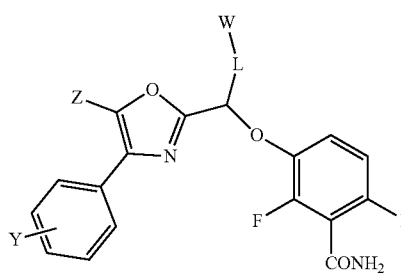

(I)

or a salt thereof, wherein:

Y is H, halo, halo($C_1$-$C_6$)alkyl, halo($C_1$-$C_6$)alkoxy, or CN;

L is a linking group;

Z is halo, cyano, or halo($C_1$-$C_6$)alkyl; and

W is a detectable group selected from the group consisting of:

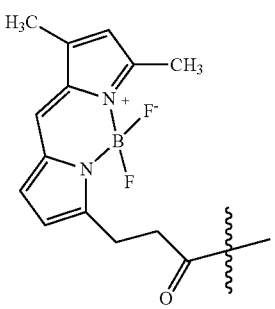

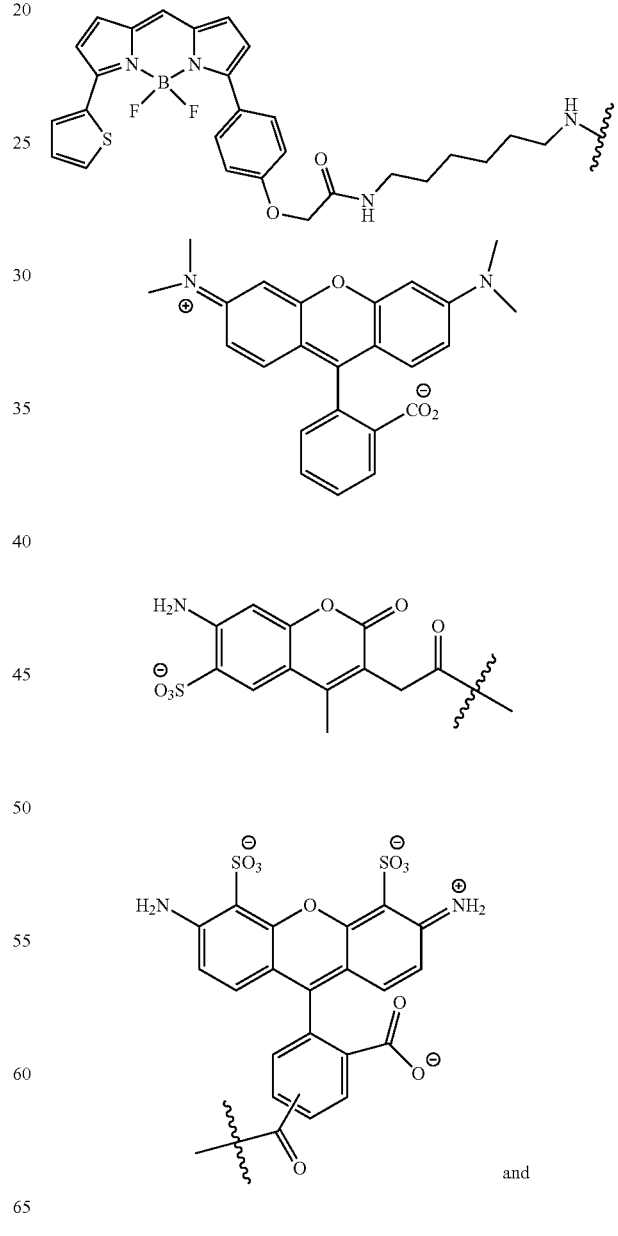

and

-continued

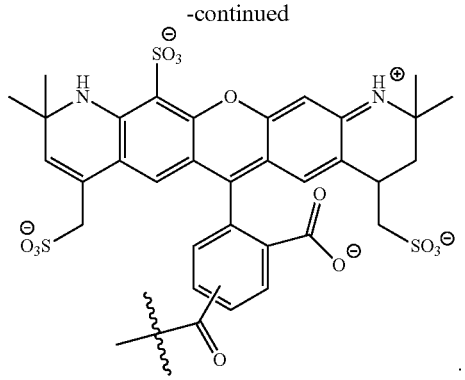

2. The compound of claim 1 wherein L comprises 3-25 atoms.

3. The compound of claim 1 wherein L is a branched or unbranched, saturated or unsaturated, hydrocarbon chain, having from 1 to 25 carbon atoms, wherein one or more of the carbon atoms are optionally replaced independently by —O—, —S—, —N($R^a$)—, 3-7 membered heterocycle, 5-6-membered heteroaryl or carbocycle and wherein each chain, 3-7 membered heterocycle, 5-6-membered heteroaryl or carbocycle is optionally and independently substituted with one or more substituents independently selected from the group consisting of ($C_1$-$C_6$)alkyl, ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, —N($R^a$)$_2$, hydroxy, oxo (=O), carboxy, aryl, aryloxy, heteroaryl, and heteroaryloxy, wherein each $R^a$ is independently H or ($C_1$-$C_6$)alkyl.

4. The compound of claim 1 wherein L is a branched or unbranched, saturated or unsaturated, hydrocarbon chain, having from 1 to 15 carbon atoms, wherein one or more of the carbon atoms is optionally replaced independently by —O— or N($R^a$)—, and wherein each carbon atom are optionally substituted with one or more substituents independently selected from the group consisting of ($C_1$-$C_6$)alkyl, ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, azido, cyano, halo, —N($R^a$)$_2$, hydroxy, oxo (=O), and carboxy, wherein each $R^a$ is independently H or ($C_1$-$C_6$)alkyl.

5. The compound of claim 1 wherein L is a branched or unbranched, saturated hydrocarbon chain, having from 1 to 15 carbon atoms, wherein one or more of the carbon atoms are optionally replaced independently by —O— or N($R^a$)—, and wherein each carbon atom is optionally substituted with one or more substituents independently selected from the group consisting of halo and oxo (=O), wherein each $R^a$ is independently H or ($C_1$-$C_6$)alkyl.

6. The compound of claim 1 wherein L is —CH$_2$CH$_2$C(=O)O—CH$_2$—, —CH$_2$C(=O)O—CH$_2$—, —C(=O)O—CH$_2$—, —O—CH$_2$—, or —CH$_2$—.

7. The compound or salt of claim 1, which is a compound of formula (Ia):

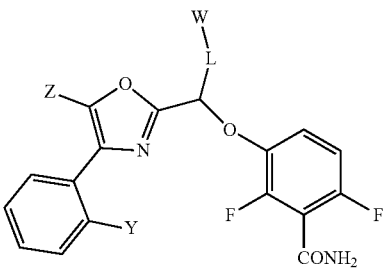

or a salt thereof.

8. The compound or salt of claim 1, which is a compound of formula (Ib):

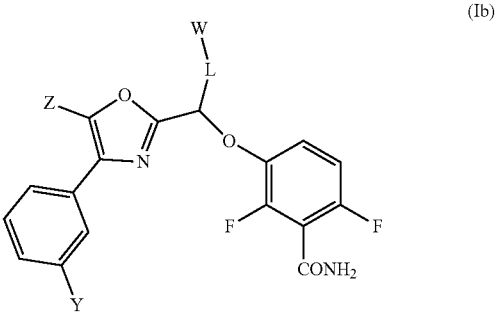

or a salt thereof.

9. The compound or salt of claim 1, which is a compound of formula (Ic):

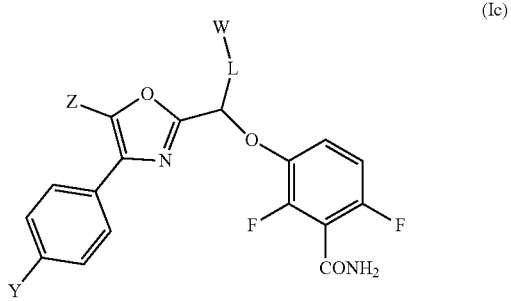

or a salt thereof.

10. The compound or salt of claim 1, which is a compound of formula (Id):

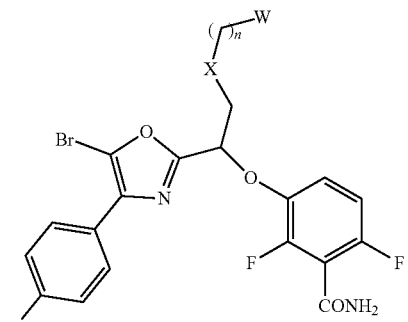

or a salt thereof, wherein:
Y is H, halo, CF$_3$, OCF$_3$, OCF$_2$CF$_3$, or CN;
X is —O—, —C(=O)—, —OC(=O)—, —C(=O)O—, —N(R$^a$)C(=O)—, —C(=O)N(R$^a$)—, —OC(=O)O—, —N(R$^a$)C(=O)O—, —OC(=O)N(R$^a$)—, —N(R$^a$)—, —S—, —SC(=O)—, —C(=O)S—, —SC(=O)O—, —O C(=O)S—, —N(R$^a$)SO$_2$—, or —SO$_2$N(R$^a$)—;
n is 0, 1, 2, 3, 4, 5, or 6; and
each R$^a$ is independently H or (C$_1$-C$_6$)alkyl.

11. The compound or salt of claim 1, which is a compound of the formula (Ie):

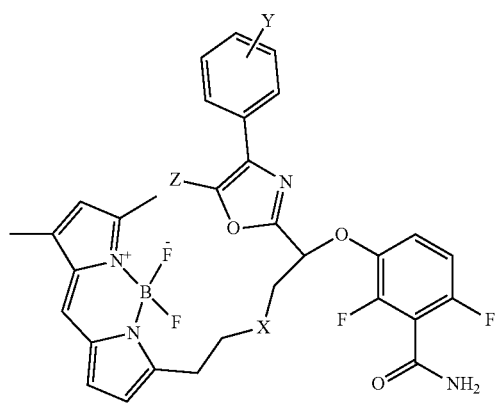

or a salt thereof, wherein X is —O—, —C(=O)—, —OC(=O)—, —C(=O)O—, —N(R$^a$)C(=O)—, —C(=O)N(R$^a$)—, —OC(=O)O—, —N(R$^a$)C(=O)O—, —OC(=O)N(R$^a$)—, —N(R$^a$)—, —S—, —SC(=O)—, —C(=O)S—, —SC(=O)O—, —O C(=O)S—, —N(R$^a$)SO$_2$—, or —SO$_2$N(R$^a$)—.

12. The compound or salt of claim 1, which is a compound of the formula (If):

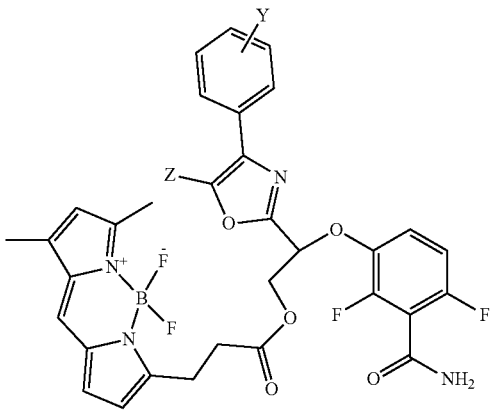

or a salt thereof.

13. The compound or salt of claim 1, which is a compound of the formula (Ig):

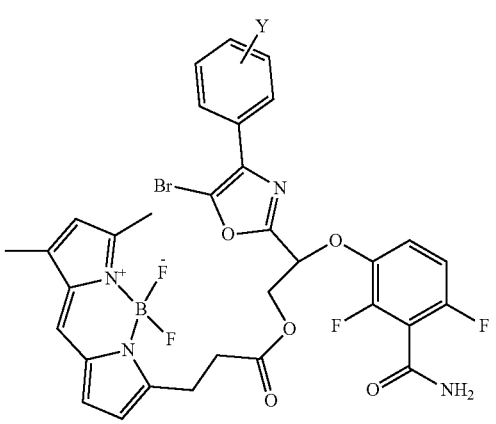

or a salt thereof.

14. The compound or salt of claim 1, which is a compound of the formula (Ih):

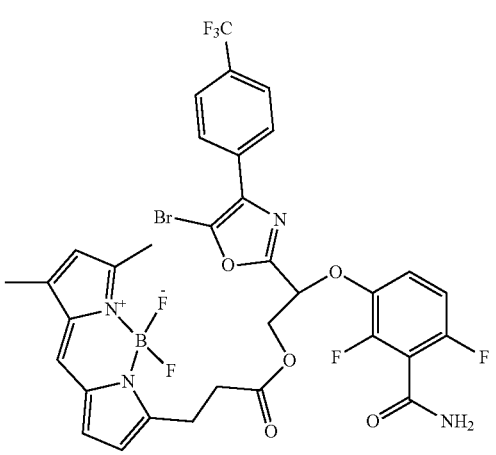

or a salt thereof.

15. A composition comprising a compound of formula (I) as described in claim 1 or a salt thereof, and a pharmaceutically acceptable excipient.

16. A method for visualizing FtsZ in live Gram-positive or Gram-negative bacterial cells comprising treating the cells with a compound of formula (I) as described in claim 1 or a salt thereof, rinsing away unreacted compound, and measuring the fluorescence of the treated cells to provide fluorescence signals, wherein the fluorescence signals are indicators of where FtsZ is located and distributed in the cells.

17. A method for monitoring cell division live Gram-positive or Gram-negative bacterial cells comprising treating the cells with a compound of formula (I) as described in claim 1 or a salt thereof, rinsing away unreacted compound, and measuring the fluorescence of the treated cells to provide fluorescence signals, wherein the fluorescence signals are indicators of where FtsZ is located and distributed in the cells.

18. A method for identifying a FtsZ inhibitor comprising treating live Gram-positive or Gram-negative bacterial cells with a test FtsZ inhibitor, followed by treatment with a compound of formula (I) as described in claim 1 or a salt thereof, rinsing away unreacted compound, and measuring the fluorescence of the treated cells to provide a fluorescence signal pattern, wherein the fluorescence signal pattern in the cells treated with the test FtsZ inhibitor characterized by an enlarged phenotype and an absence of speta or septally-localized FtsZ is indicative of FtsZ inhibition and the disruption of cell division.

* * * * *